US011504370B2

(12) United States Patent
Lee et al.

(10) Patent No.: US 11,504,370 B2
(45) Date of Patent: Nov. 22, 2022

(54) TREATMENT OF BRAIN CANCER

(71) Applicant: Array BioPharma Inc., Boulder, CO (US)

(72) Inventors: Patrice A. Lee, Boulder, CO (US); Shannon L. Winski, Boulder, CO (US); Kevin Koch, Boulder, CO (US)

(73) Assignee: ARRAY BIOPHARMA INC., Boulder, CO (US)

( * ) Notice: Subject to any disclaimer, the term of this patent is extended or adjusted under 35 U.S.C. 154(b) by 0 days.

(21) Appl. No.: 16/402,068

(22) Filed: May 2, 2019

(65) Prior Publication Data

US 2019/0255051 A1 Aug. 22, 2019

Related U.S. Application Data

(63) Continuation of application No. 14/387,533, filed as application No. PCT/US2013/033751 on Mar. 25, 2013, now abandoned.

(60) Provisional application No. 61/615,082, filed on Mar. 23, 2012.

(51) Int. Cl.
*A61K 31/517* (2006.01)
*A61P 35/04* (2006.01)
*A61P 35/00* (2006.01)
*A61K 31/337* (2006.01)
*A61K 31/7068* (2006.01)
*A61K 45/06* (2006.01)

(52) U.S. Cl.
CPC .......... *A61K 31/517* (2013.01); *A61K 31/337* (2013.01); *A61K 31/7068* (2013.01); *A61K 45/06* (2013.01); *A61P 35/00* (2018.01); *A61P 35/04* (2018.01)

(58) Field of Classification Search
CPC .............. A61K 31/517; A61K 2300/00; A61K 31/337; A61K 31/7068; A61K 45/06; A61P 35/00; A61P 35/04
See application file for complete search history.

(56) References Cited

U.S. PATENT DOCUMENTS

| 6,127,350 | A | 10/2000 | Niesor et al. | |
|---|---|---|---|---|
| 8,648,087 | B2 | 2/2014 | Lyssikatos et al. | |
| 9,168,254 | B2 | 10/2015 | Corson et al. | |
| 9,457,093 | B2 * | 10/2016 | Fry | A61K 9/2009 |
| 9,693,989 | B2 | 7/2017 | Lyssikatos et al. | |
| 9,889,134 | B2 * | 2/2018 | Corson | C07D 471/04 |
| 10,143,692 | B2 * | 12/2018 | Corson | C07D 471/04 |
| 2002/0137731 | A1 | 9/2002 | Gewirtz | |
| 2014/0023643 | A1 | 1/2014 | Lyssikatos et al. | |
| 2014/0296267 | A1 | 10/2014 | Fry et al. | |
| 2015/0110780 | A1 | 4/2015 | Lee et al. | |
| 2017/0136022 | A1 | 5/2017 | Fry et al. | |
| 2017/0252317 | A1 | 9/2017 | Lyssikatos et al. | |
| 2018/0271824 | A1 | 9/2018 | Lyssikatos et al. | |
| 2019/0125749 | A1 | 5/2019 | Corson et al. | |
| 2019/0275043 | A1 | 9/2019 | Fry et al. | |

FOREIGN PATENT DOCUMENTS

| CO | 14103943 | | 5/2014 |
|---|---|---|---|
| EP | 0988863 | A2 | 3/2000 |
| EP | 1971601 | B1 | 10/2009 |
| WO | 2005016346 | A1 | 2/2005 |
| WO | 2005120504 | A2 | 12/2005 |
| WO | 2007059257 | A2 | 5/2007 |
| WO | 2007117749 | A2 | 10/2007 |
| WO | 2009042618 | A1 | 4/2009 |
| WO | 2009117277 | A2 | 9/2009 |
| WO | 2013142875 | A1 | 9/2013 |

OTHER PUBLICATIONS

Melisko et al. (Nature Clinical Practice Oncology, Jan. 2009 vol. 6, No. 1) (Year: 2009).*
Moulder et al. "ARRY-380, a Selective HER2 Inhibitor: From Drug Design to Clinical Evaluation," Abstract #A143, AACR-NCI-EORTC, Nov. 12-16, 2011, San Francisco, CA, (Year: 2011).*
Koch "ARRY-380: A Selective, Oral HER2 Inhibitor for the Treatment of Solid Tumors," Apr. 3, 2011, pp. 1-29 (Year: 2011).*
Walpole et al. BMC Public Health 2012, 12:439. (Year: 2012).*
Japanese Office Action for Application No. 2019-034250, 3 pages, dated Jan. 15, 2020.
Sorges, Virgina , et al., "A phase 1b study of ONT-380, an oral HER2-specific inhibitor, combined with ado-trastuzumab emtansine (T-DM1), in HER2+ metastatic breast cancer (MBC)", Full Poster along with enlarged sections of full poster, American Society of Clinical Oncology, Annual Meeting 2014, Poster Board #121 A, Abstract ID TPS662, 6 pages, Jun. 2, 2014.
Borges, Virgina , et al., "ONT-380 (ARRY-380)—an Oral HER2 Inhibitor—Final Phase 1 Results and Conclusions", Full Poster along with enlarged sections of full poster, AACR Advances in Breast Cancer Research: Genetics, Biology and Clinical Applications, Poster# A050, 9 pages, Oct. 4, 2013.
Colombian Office Action , issued in corresponding Colombian Application No. 14-208.829, 10 pages, dated Jun. 23, 2015.
Dinkel, Victoria, et al., "ARRY-380, a potent, small molecule inhibitor of ErbB2, increases survival in intracranial ErbB2+ xenograft models in mice", Full Poster along with enlarged sections of full poster, American Association for Cancer Research, 8 pages, Apr. 1, 2012.
Ferrario, Cristiano , et al., "A Phase 1b Study of ONT-380, an Oral HER2-Specific Inhibitor, Combined with Ado-Trastuzumab Emtansine (T-DM1), in HER2+ Metastatic Breast Cancer (MBC)", Full Poster along with enlarged sections of full poster, San Antonio Breast Cancer Symposium, Program # P4-14-20, 17 pages, Dec. 11, 2015.
Ferrario, Cristiano , et al., "ONT-380 in the Treatment of HER2+ Breast Cancer Central Nervous System (CNS) Metastases (Mets)", American Society of Clinical Oncology Annual Meeting, Abstract/Poster No. 612. May 30, 2015.

(Continued)

*Primary Examiner* — Kortney L. Klinkel
*Assistant Examiner* — William Y Lee
(74) *Attorney, Agent, or Firm* — Viksnins Harris Padys Malen LLP

(57) ABSTRACT

Compounds for the treatment of brain cancer are provided herein. Pharmaceutical compositions comprised of those compounds for the treatment of brain cancer are also provided herein.

16 Claims, 7 Drawing Sheets

(56) References Cited

OTHER PUBLICATIONS

Friesen, D., et al., "Hydroxypropyl Methylcellulose Acetate Succinate-Based Spray-Dried Dispersions: An Overview", Molecular Pharmaceutics, vol. 5, No. 8, 1003-1019 (2008).
Hamilton, Erika, et al., "A Phase 1b Study of ONT-380, an Oral HER2-Specific Inhibitor in Combination with Capecitabine (C) and Trastuzumab (T) in 3rd Line+ Treatment of HER2+ Metastatic Breast Cancer (MBC)", Full Poster along with enlarged sections of full poster, American Society of Clinical Oncology Annual Meeting, Abstract/Poster No. 302, 5 pages, May 30, 2015.
Hamilton, Erika, et al., "A phase 1b study of ONT-380, an oral ONT HER2-specific inhibitor, combined with capecitabine and trastuzumab, in HER2+ metastatic breast cancer (MBC)", American Society of Clinical Oncology, Annual Meeting 2014, Poster Board #121B, Abstract ID: TPS663. Jun. 2, 2014.
Koch, K , "Arry 380: A Selective, Oral HER2 Inhibitor for the Treatment of Solid Tumors", American Association of Cancer Research 102nd Annual Meeting, 29 pages, Apr. 3, 2011.
Lee, Patrice , et al., "In Vivo Activity of ARRY-380, a Potent, Small Molecule Inhibitor of ErbB2 in Combination with Trastuzumab or Docetaxel in BT-474 Human Breast Carcinoma Xenograft Model", Full Poster along with enlarged sections of full poster, American Association for Cancer Research, Poster #5581, 10 pages, Apr. 18-22, 2009.
Lee, Patrice , et al., "In Vivo Activity of ARRY-380, a Potent, Small Molecule Inhibitor of ErbB2 in Combination with Trastuzumab, Docetaxel or Bevacizumab", Full Poster along with enlarged sections of full poster, San Antonio Breast Cancer Symposium, Poster #510, 11 pages, Dec. 9-13, 2009.
Lindemann, C., et al., "Amorphous Dispersion Development of ARRY-380, an ErbB2 Selective Inhibitor", American Association of Pharmaceutical Scientists, Annual Meeting and Exposition. Oct. 17, 2012.
Lindemann, C., et al., "Solid-State Characterization of Seven Isomorphic Solvates of ARRY-380", Full Poster along with enlarged sections of full poster, American Association of Pharmaceutical Scientists, Annual Meeting and Exposition, 5 pages, Oct. 17, 2012.
Melisko , et al., "New Challenges and opportunities in the management of brain metastases in patients with ErbB2-positive metastatic breast cancer", Nature Clinical Practice Oncology, vol. 6 (1), 25-33 (2009).
Morrow, PK , et al., "A Phase 1 Study to Assess the Safety, Tolerability and PK of ARRY-380—an Oral Inhibitor of HER2", American Society of Clinical Oncologists, Poster #A7. Oct. 1, 2010.
Moulder, et al., "ARRY-380, a Selctive HER2 Inhibitor: From Drug Design to Clinical Evaluation", AACR-NCI-EORTC International Conference: Molecular Targets and Cancer Therapeutics, Abstract #A143. Nov. 14, 2011.
Moulder, SL , et al., "Data from a Completed Phase 1 Study to Assess the Safety, Tolerability and PK of ARRY-380—an Oral Inhibitor of HER2", San Antonio Breast Cancer Symposium, Program # P3-14-07. Dec. 10, 2010.
Murthy, Rashmi Krishna , et al., "ONT-380 in the Treatment of HER2+ Breast Cancer Central Nervous System (CNS) Metastases", Full Poster along with enlarged sections of full poster, San Antonio Breast Cancer Symposium, Program # P4-14-19, 14 pages, Dec. 11, 2015.
Okamoto, H., et al., "PSWC2004 Symposium Report on Pharmaceutical Field", Pharm Tech Japan, vol. 20, No. 9 1783-1785, 1958(2004).
Patent Cooperation Treaty, International Searching Authority, Search Report and Written Opinion for PCT/US2013/033751, 10 pages, Jun. 5, 2013.
Pheneger, Tracy, et al., "In Vitro and In Vivo Activity of ARRY-380: a Potent, Small Molecule Inhibitor of ErbB2", Full Poster along with enlarged sections of full poster, American Association for Cancer Research, #1795, 11 pages, Apr. 18-22, 2009.
Qian, F , et al., "Drug-polymer solubility and miscibility: Stability consideration and practical challenges in amorphous solid dispersion development", Journal of Pharmaceutical Sciences 99, 2941-2947 (2010).
Chinese Office Action for CN Application No. 2018111509189, with English Translation, 15 pages, dated Dec. 30, 2020.
Shengnan, M , Pharmaceutics, 252-256 (2012). [Non-English Document].
Asco , "FDA Grants Breakthrough Therapy Designation to Tucatinib in Combination Therapy for HER2-Postive Breast Cancer", https://ascopost.com/issues/january-25-2020/fda-grants-breakthrough-therapy-designation-to-tucatinib-in-combination-therapy-for-her2-positive-breast-cancer/, 3 pages (2020).
healio.com , "FDA grants priority review to tucatinib for HER2-positive breast cancer", https://www.healio.com/news/hematology-oncology/20200213/fda-grants-priority-review-to-tucatinib-for-her2positive-breast-cancer, 2 pages (2020).
Jacob, S , et al., "Solid state crystallinity, amorphous state, and its implications in the pharmaceutical process", IJPSR 2(3), 472-482 (2011).
Lin, N , et al., "Intracranial Efficacy and Survival With Tucatinib Plus Trastuzumab and Capecitabine for Previously Treated HER2-Positive Breast Cancer with Brain Metastases in the HER2CLIMB Trial", J Clin Oncol 38, 2610-2619 (2020).
Murthy, R , et al., "Tucatinib, Trastuzumab, and Capecitabine for HER2-Postive Metastatic Breast Cancer", The New England Journal of Medicine 382(7), 597-609 (2020).
Vasconcelos , et al., "Solid dispersions as strategy to improve oral bioavailability of poor water soluble drugs", Drug Discovery Today, vol. 12 (23-24), 1068-1075 (2007).
Vo, A , et al., "Clinical pharmacokinetics of an improved tablet formulation of ONT-380 in HER2+metastatic breast cancer patients", Proceedings of the AACR-NCI-EORTC International Conference: MolecularTargets and CancerTherapeutics; Boston, MA. Philadelphia (PA) (Nov. 5-9, 2015): AACR; Mol CancerTher 14 (12 Suppl) (2015). 2):Abstract nrB152.
Dinkel, V, et al., "Abstract 852: ARRY-380, a Potent, Small Molecule Inhibitor of ErbB2, Increases Survival in Intracranial ErbB2+ Xenograft Models in Mice", Proceedings of the 103rd Annual Meeting of the American Association tor Cancer Research; Chicago, IL, Philadelphia (PA), 4 pages, Mar. 31, 2012-Apr. 4, 2012: AACR, Cancer Res 72 (8 Suppl) Abstract nr 852. doi:1538-7445. AM2012-852m (2012).
Kumar Giri, T, et al., "A novel and alternative approach to controlled release drug delivery system based on solid dispersion technique", Bulletin of Faculty of Pharmacy, Cairo University 50, 147-159 (2012).
Srinarong, P, et al., "Improved dissolution behavior of lipophilic drugs by solid dispersions: the production process as starting point for formulation considerations", Expert Opinion on Drug Delivery 8(9), 1121-1140 (2011).
Zielinski, C, et al., "Optimising the dose of capecitabine in metastatic breast cancer: confused, clarified or confirmed?". Annals of Oncology 21, 2145-2152 (2010).

* cited by examiner

TREATMENT OF BRAIN CANCER

CROSS-REFERENCE TO RELATED APPLICATIONS

This application is a Continuation of U.S. patent application Ser. No. 14/387,533, filed Sep. 23, 2014, which is a 35 U.S.C. § 371 application of International Patent Application No. PCT/US2013/033751, filed Mar. 25, 2013 and claims the benefit of U.S. Provisional Application No. 61/615,082, filed Mar. 23, 2012. The entire content of the applications referenced above are hereby incorporated by reference herein.

BACKGROUND OF THE INVENTION

Field of the Invention

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine for the treatment of brain cancer is provided herein.

Description of the State of the Art

N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine (also called "ARRY-380"), which has the structure:

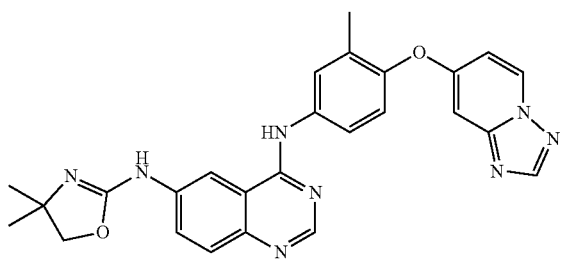 [SMILES: Cc1cc(Nc2ncnc3ccc(NC4=NC(C)(C)CO4)cc23)ccc1Oc1ccn2ncnc2c1]

is a selective ErbB2 (HER2) inhibitor described in WO 2007/059257, which is incorporated by reference in its entirety. N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine has been tested in human clinical trials for hyperproliferative diseases, particularly cancer, and more particularly metastatic breast cancer, colorectal cancer, and salivary gland cancer (see Koch, Kevin. "ARRY-380: A Selective, Oral HER2 Inhibitor for the Treatment of Solid Tumors." American Association of Cancer Research 102$^{nd}$ Annual Meeting, Apr. 3, 2011; which may also be found at: http://www.arraybiopharma.com/_documents/Publication/PubAttachment462.pdf).

Amplification or over-expression of ErbB2 has been shown to play a role in the pathogenesis and progression of certain cancers, such as breast, ovarian, gastric, uterine, colorectal and non-small cell lung cancer.

In breast cancer patients, brain metastases are a leading cause of death in ErbB2+ breast cancer patients and a serious unmet medical need. Patients with ErbB2+ breast cancer have a significantly increased incidence of brain metastases following trastuzumab therapy. There is an increasing incidence of brain metastases as women are living longer due to better treatments for systemic disease.

Accordingly, there remains a need for the treatment of brain cancer.

SUMMARY OF THE INVENTION

One aspect of the present invention provides N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for use in treating brain cancer.

Another aspect provides a method of treating brain cancer in a mammal comprising administering a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol to the mammal.

Another aspect provides a method of treating brain cancer in a patient having brain cancer comprising administering a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol to the patient.

Another aspect provides a method of treating or preventing brain cancer in a mammal in need of such treatment, wherein the method comprises administering to said mammal a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol.

Another aspect provides a use of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol in the manufacture of a medicament for the treatment of brain cancer.

Another aspect provides a pharmaceutical composition for the treatment of brain cancer, comprising N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof.

DETAILED DESCRIPTION OF THE INVENTION

Figure 1:
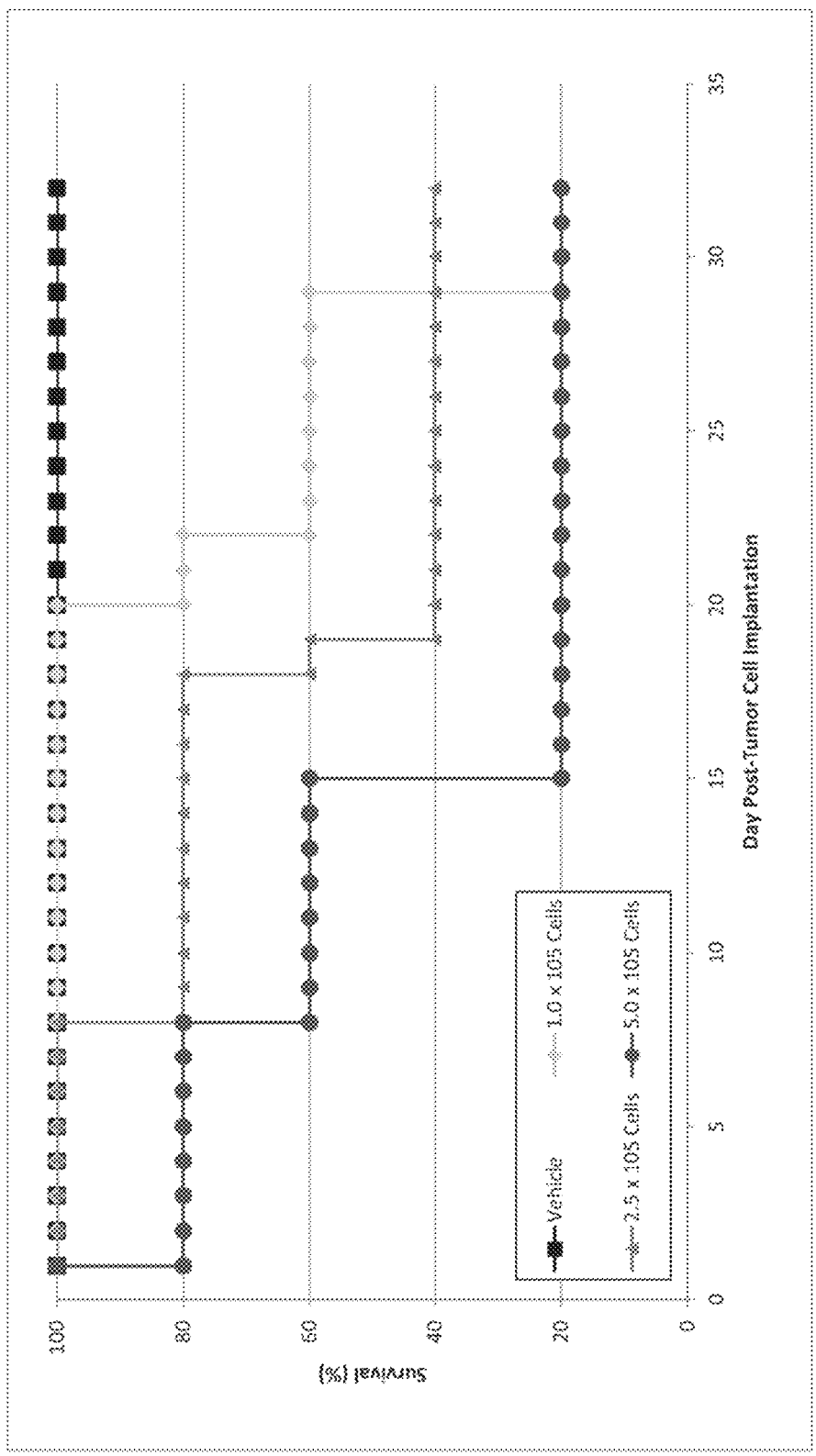
FIG. 1 shows the results of the growth of NCI-N87 cells implanted intracranially in mice.

Reference will now be made in detail to certain embodiments. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. In the event that one or more of the incorporated literature and similar materials differs from or contradicts this application, including but not limited to defined terms, term usage, described techniques, or the like, this application controls.

Definitions

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "amorphous" means a solid in a solid state that is a non-crystalline state. Amorphous solids generally possess crystal-like short range molecular arrangement, but no long range order of molecular packing as found in crystalline solids. The solid state form of a solid may be determined by polarized light microscopy, x-ray powder diffraction, differential scanning calorimetry, or other standard techniques known to those of skill in the art.

The phrase "amorphous solid dispersion" means a solid comprising a drug substance and a dispersion polymer. The amorphous solid dispersion discussed herein comprises amorphous N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol as the drug substance component and a dispersion polymer, wherein the amorphous solid dispersion contains the drug substance component in a substantially amorphous solid state form. In certain embodiments, the substantially amorphous solid state form means at least 80% amorphous drug substance component. In certain embodiments, the substantially amorphous solid state form means at least 85% drug substance component. In certain embodiments, the substantially amorphous solid state form means at least 90% amorphous drug substance component. In certain embodiments, the substantially amorphous solid state form means at least 95% amorphous drug substance component.

The phrase "dispersion polymer" means a polymer that allows for N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol to be dispersed throughout such that a solid dispersion may form. The dispersion polymer is preferably neutral or basic. The dispersion polymer may contain a mixture of two or more polymers. Examples of dispersion polymers include, but are not limited to, vinyl polymers and copolymers, vinylpyrrolidine vinylacetate copolymer ("PVP-VA"), polyvinyl alcohols, polyvinyl alcohol polyvinyl acetate copolymers, polyvinyl pyrrolidine ("PVP"), acrylate and methacrylate copolymers, methylacrylic acid methyl methacrylate copolymer (such as Eudragit®), polyethylene polyvinyl alcohol copolymers, polyoxyethylene-polyoxypropylene block copolymers (also referred to as poloxamers), graft copolymer comprised of polyethylene glycol, polyvinyl caprolactam and polyvinyl acetate (such as Soluplus®), cellulosic polymers, such as hydroxypropyl methyl cellulose acetate ("HPMCA"), hydroxypropyl methyl cellulose ("HPMC"), hydroxypropyl cellulose ("HPC"), methyl cellulose, hydroxyethyl methyl cellulose, hydroxyethyl cellulose, hydroxyethyl cellulose acetate, and hydroxyethyl ethyl cellulose, hydroxypropyl methyl cellulose acetate succinate ("HPMCAS"), hydroxypropyl methyl cellulose phthalate ("HPMCP"), carboxymethylethyl cellulose ("CMEC"), cellulose acetate phthalate ("CAP"), cellulose acetate succinate ("CAS"), hydroxypropyl methyl cellulose acetate phthalate ("HPMCAP"), cellulose acetate trimellitate ("CAT"), hydroxypropyl methyl cellulose acetate trimellitate ("HPMCAT"), and carboxymethylcellulose acetate butyrate ("CMCAB"), and the like.

The term "drug substance component" means the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol component of the solid dispersion.

The term "mammal" means a warm-blooded animal that has or is at risk of developing a disease described herein and includes, but is not limited to, guinea pigs, dogs, cats, rats, mice, hamsters, and primates, including humans.

The phrase "pharmaceutically acceptable" indicates that the substance or composition is compatible chemically and/or toxicologically, with the other ingredients comprising a formulation, and/or the mammal being treated therewith.

The phrase "solid dispersion" means a system in a solid state comprising at least two components, wherein one component is dispersed throughout the other component. The solid dispersion discussed herein comprises one component of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-]pyridin-7-yloxy)-3-methylphenyl)amino)quinazolin-6-yl)amino)-4-methyl-4,5-dihydrooxazol-4-yl)methanol, the drug substance component, dispersed throughout another component, particularly a dispersion polymer.

The phrase "spray drying" means processes involved in breaking up liquid mixtures into small droplets (atomization) and rapidly removing solvent from the mixture in a spray drying apparatus where there is a strong driving force for evaporation of solvent from the droplets. The phrase spray drying is used conventionally and broadly. Spray drying processes and spray drying equipment are described generally in Perry, Robert H., and Don W. Green (eds.). *Perry's Chemical Engineers' Handbook*. New York: McGraw-Hill, 2007 (8$^{th}$ edition).

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Treatment of Brain Cancer

Provided herein is N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine for use in treating brain cancer.

It has been found that (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol (also called "AR00440993"), which has the structure:

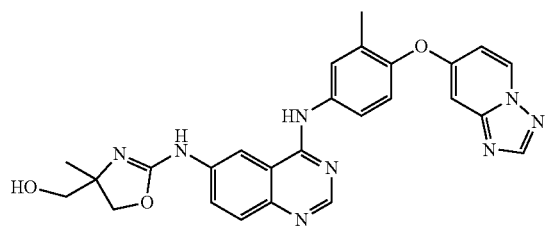 [SMILES: Cc1cc(Nc2ncnc3ccc(NC4=NC(C)(CO)CO4)cc23)ccc1Oc1ccn2ncnc2c1]

is an active metabolite of ARRY-380. (2-((4-((4-([1,2,4]Triazolo[1,5-a]pyridin-7-yloxy)-3-methylphenyl)amino)quinazolin-6-yl)amino)-4-methyl-4,5-dihydrooxazol-4-yl)methanol has higher brain penetration than either ARRY-380 or lapatinib (see Example 1). This active metabolite helps maintain sustained levels of drug in the brain after oral dosing of ARRY-380, which may contribute to enhanced activity.

In certain embodiments, N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine for use in the treatment of brain cancer is provided.

In certain embodiments, (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for use in the treatment of brain cancer is provided.

In certain embodiments, N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for use in the treatment of brain cancer are provided.

In certain embodiments, (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for use in the treatment of brain cancer comprising administering N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is provided.

Brain cancer includes anaplastic astrocytoma, anaplastic mixed glioma, anaplastic oligoastrocytoma, anaplastic oligodendroglioma, germinoma, glioblastoma multiforme, gliosarcoma, low grade astrocytoma, low grade mixed oligoastrocytoma, low grade oligodendroglioma, central nervous system lymphoma, medulloblastoma, meningioma, pilocytic astrocytoma, acoustic neuroma, chordoma, craniopharyngioma, brain stem glioma, ependymoma, optic nerve glioma, subependymoma, metastaic brain tumors, pituitary tumors, primitive neuroectodermal and scwannoma.

In certain embodiments, the brain cancer is local or metastatic brain cancer that is ErbB2 driven. In certain embodiments, the brain cancer is local or metastatic brain cancer that is driven by ErbB2. In certain embodiments, the brain cancer is local or metastatic brain cancer that is caused by ErbB2 over-expression and amplification. In certain embodiments, the brain cancer is local or metastatic brain cancer that is caused by ErbB2 over-expression or amplification. In certain embodiments, the brain cancer is local or metastatic brain cancer that is caused by ErbB2 over-expression. In certain embodiments, the brain cancer is local or metastatic brain cancer that is caused by ErbB2 amplification. In certain embodiments, the brain cancer is local or metastatic brain cancer that is ErbB2 positive.

Brain cancer includes gliomas, meningiomas, pituitary adenomas and nerve sheath tumors. Brain cancer also includes anaplastic astrocytoma, anaplastic mixed glioma, anaplastic oligoastrocytoma, anaplastic oligodendroglioma, germinoma, glioblastoma multiforme, gliosarcoma, low grade astrocytoma, low grade mixed oligoastrocytoma, low grade oligodendroglioma, central nervous system lymphoma, medulloblastoma, meningioma (particularly WHO Grade II and III), and pilocytic astrocytoma. Brain cancer also includes acoustic neuroma, pilocytic astrocytoma (WHO Grade I), low-grade astrocytoma (WHO Grade II), anaplastic astrocytoma (WHO Grade III), glioblastoma multiforme (WHO Grade IV), chordoma, central nervous system lymphoma, craniopharyngioma, brain stem glioma, ependymoma, mixed glioma, optic nerve glioma, subependymoma, medulloblastoma, meningioma, metastaic brain tumors, oligodendroglioma, pituitary tumors, primitive neuroectodermal, and scwannoma. In certain embodiments, the brain cancer is ErbB2 positive. In certain embodiments, the brain cancer is caused by ErbB2 over-expression or amplification.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine for use in the treatment of brain cancer is administered from about 0.1 to about 2000 mg per day. The total dose need not be administered all at once. In certain embodiments, the administration is from about 25 to about 1600 mg per day. In certain embodiments, the administration is from about 100 to about 1600 mg per day. In certain embodiments, the administration is from about 800 to about 1600 mg per day. In certain embodiments, the administration is at 800 to 1600 mg per day. In certain embodiments, the administration is from about 800 to about 1300 mg per day. In certain embodiments, the administration is at 800 to 1300 mg per day. In certain embodiments, the administration is from about 1100 to about 1300 mg per day. In certain embodiments, the administration is at 1100 to 1300 mg per day. In certain embodiments, the administration is from about 1200 to about 1300 mg per day. In certain embodiments, the administration is at 1200 to 1300 mg per day. In certain embodiments, the administration is from about 1200 mg per day. In certain embodiments, the administration is at 1200 mg per day.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine for the treatment of brain cancer is administered from about 400 to about 800 mg twice per day. In certain embodiments, the administration is at 400 to 800 mg twice per day. In certain embodiments, the administration is from about 400 to about 650 mg twice per day. In certain embodiments, the administration is at 400 to 650 mg twice per day. In certain embodiments, the administration is from about 550 to about 650 mg twice per day. In certain embodiments, the administration is at 550 to 650 mg twice per day. In certain embodiments, the administration is from about 600 to about 650 mg twice per day. In certain embodiments, the administration is at 600 to 650 mg twice per day. In certain embodiments, the administration is at about 600 mg twice per day. In certain embodiments, the administration is at 600 mg twice per day.

In certain embodiments, the (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for the treatment of brain cancer is administered from about 0.1 to about 2000 mg per day. The total dose need not be administered all at once. In certain embodiments, the administration is from about 25 to about 1800 mg per day. In certain embodiments, the administration is from about 25 to about 1600 mg per day. In certain embodiments, the administration is from about 100 to about 1800 mg per day. In certain embodiments, the administration is from about 100 to about 1600 mg per day. In certain embodiments, the administration is from about 800 to about 1600 mg per day. In certain embodiments, the administration is at 800 to 1600 mg per day. In certain embodiments, the administration is from about 800 to about 1300 mg per day. In certain embodiments, the administration at 800 to 1300 mg per day. In certain embodiments, the administration is from about 1100 to about 1300 mg per day. In certain embodiments, the administration is at 1100 to 1300 mg per day. In certain embodiments, the administration is from about 1200 to about 1300 mg per day. In certain embodiments, the administration is at 1200 to 1300 mg per day. In certain embodiments, the administration is at about 1200 mg per day. In certain embodiments, the administration is at 1200 mg per day.

In certain embodiments, the (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for the treatment of brain cancer is administered from about 100 to about 1000 mg twice per day. In certain embodiments, the administration is from about 100 to about 800 mg twice per day. In certain embodiments, the administration is from about 100 to about 750 mg twice per day. In certain embodiments, the administration is from about 100 to about 600 mg twice per day. In certain embodiments, the administration is from about 200 to about 800 mg twice per day. In certain embodiments, the administration is from about 400 to about 800 mg twice per day. In certain embodiments, the administration is at 400 to 800 mg twice per day. In certain embodiments, the administration is from about 400 to about 650 mg twice per day. In certain embodiments, the administration is at 400 to 650 mg twice per day. In certain embodiments, the administration is from about 550 to about 650 mg twice per day. In certain embodiments, the administration is at 550 to 650 mg twice per day. In certain embodiments, the administration is from about 600 to about 650 mg twice per day. In certain embodiments, the administration is at 600 to 650 mg twice per day. In certain embodiments, the administration is at about 600 mg twice per day. In certain embodiments, the administration is at 600 mg twice per day.

In certain embodiments, the mixture of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for the treatment of brain cancer is administered from about 0.1 to about 2000 mg per day. The total dose need not be administered all at once. In certain embodiments, the administration is from about 25 to about 1800 mg per day. In certain embodiments, the administration is from about 25 to about 1600 mg per day. In certain embodiments, the administration is from about 100 to about 1800 mg per day. In certain embodiments, the administration is from about 100 to about 1600 mg per day. In certain embodiments, the administration is from about 800 to about 1600 mg per day. In certain embodiments, the administration is at 800 to 1600 mg per day. In certain embodiments, the administration is from about 800 to about 1300 mg per day. In certain embodiments, the administration is at 800 to 1300 mg per day. In certain embodiments, the administration is from about 1100 to about 1300 mg per day. In certain embodiments, the administration is at 1100 to 1300 mg per day. In certain embodiments, the administration is from about 1200 to about 1300 mg per day. In certain embodiments, the administration is at 1200 to 1300 mg per day. In certain embodiments, the administration is at about 1200 mg per day. In certain embodiments, the administration is at 1200 mg per day.

In certain embodiments, the mixture of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol for the treatment of brain cancer is administered from about 100 to about 1000 mg twice per day. In certain embodiments, the administration is from about 100 to about 800 mg twice per day. In certain embodiments, the administration is from about 100 to about 750 mg twice per day. In certain embodiments, the administration is from about 100 to about 600 mg twice per day. In certain embodiments, the administration is from about 200 to about 800 mg twice per day. In certain embodiments, the administration is from about 400 to about 800 mg twice per day. In certain embodiments, the administration is at 400 to 800 mg twice per day. In certain embodiments, the administration is from about 400 to about 650 mg twice per day. In certain embodiments, the administration is at 400 to 650 mg twice per day. In certain embodiments, the administration is from about 550 to about 650 mg twice per day. In certain embodiments, the administration is at 550 to 650 mg twice per day. In certain embodiments, the administration is from about 600 to about 650 mg twice per day. In certain embodiments, the administration is at 600 to 650 mg twice per day. In certain embodiments, the administration is at about 600 mg twice per day. In certain embodiments, the administration is at 600 mg twice per day.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-

([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for the treatment of brain cancer is administered as an oral dosage form.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for the treatment of brain cancer is provided in a solid dispersion dosage form. In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for the treatment of brain cancer is provided in a solid dispersion oral dosage form.

Solid dispersions are generally prepared by dissolving the drug substance and the dispersion polymer in a suitable solvent to form a feed solution, and then the feed solution may be spray dried to form the solid dispersion (and remove the solvent). Spray drying is a known process. Spray drying is generally performed by dissolving the drug substance component and the dispersion polymer in a suitable solvent to prepare a feed solution. The feed solution may be pumped through an atomizer into a drying chamber. The feed solution can be atomized by conventional means known in the art, such as a two-fluid sonicating nozzle, a pressure nozzle, a rotating nozzle and a two-fluid non-sonicating nozzle. Then, the solvent is removed in the drying chamber to form the solid dispersion. A typical drying chamber uses hot gases, such as forced air, nitrogen, nitrogen-enriched air, or argon to dry particles. The size of the drying chamber may be adjusted to achieve particle properties or throughput.

Although the solid dispersion are preferably prepared by conventional spray drying techniques, other techniques known in the art may be used, such as melt extrusion, freeze drying, rotary evaporation, drum drying or other solvent removal processes.

In certain embodiments, the dispersion polymer is selected from PVP-VA, methylacrylic acid methyl methacrylate copolymer, HPMCP, CAP, HPMCAS and HPMC and mixtures thereof. In certain embodiments, the dispersion polymer is selected from PVP-VA, methylacrylic acid methyl methacrylate copolymer, HPMCP, CAP, HPMCAS and HPMC. In certain embodiments, the dispersion polymer is selected from PVP-VA, Eudragit® L100, HPMCP H-55, CAP, HPMCAS Grade M, HPMC and mixtures thereof. In certain embodiments, the dispersion polymer is selected from PVP-VA, Eudragit® L100, HPMCP H-55, CAP, HPMCAS Grade M and HPMC.

In certain embodiments, the dispersion polymer is selected from PVP-VA, methylacrylic acid methyl methacrylate copolymer, HPMCP, CAP and HPMCAS, and mixtures thereof. In certain embodiments, the dispersion polymer is selected from PVP-VA, methylacrylic acid methyl methacrylate copolymer, HPMCP, CAP and HPMCAS. In certain embodiments, the dispersion polymer is selected from PVP-VA, Eudragit® L100, HPMCP H-55, CAP and HPMCAS Grade M, and mixtures thereof. In certain embodiments, the dispersion polymer is selected from PVP-VA, Eudragit® L100, HPMCP H-55, CAP and HPMCAS Grade M.

In certain embodiments, the dispersion polymer is selected from PVP-VA, methylacrylic acid methyl methacrylate copolymer, HPMCP, CAP and HPMC, and mixtures thereof. In certain embodiments, the dispersion polymer is selected from PVP-VA, methylacrylic acid methyl methacrylate copolymer, HPMCP, CAP and HPMC. In certain embodiments, the dispersion polymer is selected from PVP-VA, Eudragit® L100, HPMCP H-55, CAP and HPMC, and mixtures thereof. In certain embodiments, the dispersion polymer is selected from PVP-VA, Eudragit® L100, HPMCP H-55, CAP and HPMC.

In certain embodiments, the dispersion polymer is selected from PVP-VA, methylacrylic acid methyl methacrylate copolymer, HPMCP and CAP, and mixtures thereof. In certain embodiments, the dispersion polymer is selected from PVP-VA, methylacrylic acid methyl methacrylate copolymer, HPMCP and CAP. In certain embodiments, the dispersion polymer is selected from PVP-VA, Eudragit® L100, HPMCP H-55 and CAP, and mixtures thereof. In certain embodiments, the dispersion polymer is selected from PVP-VA, Eudragit® L100, HPMCP H-55 and CAP.

In certain embodiments, the dispersion polymer is PVP-VA.

In certain embodiments, the dispersion polymer is methylacrylic acid methyl methacrylate copolymer. In certain embodiments, the dispersion polymer is Eudragit®. In certain embodiments, the dispersion polymer is Eudragit® L100.

In certain embodiments, the dispersion polymer is HPMCP. In certain embodiments, the dispersion polymer is HPMCP H-55.

In certain embodiments, the dispersion polymer is CAP.

In certain embodiments, the dispersion polymer is HPMCAS. In certain embodiments, the dispersion polymer is HPMCAS Grade M.

In certain embodiments, the dispersion polymer is preferably neutral or basic. In certain embodiments, the dispersion polymer is selected from PVP-VA and HPMC. In certain embodiments, the dispersion polymer is HPMC.

Suitable solvents are a solvent or mixture of solvents in which both drug substance component and the dispersion polymer have adequate solubility (solubility greater than 1 mg/mL). A mixture of solvents may be used if each component of the solid dispersion (i.e., drug substance component and dispersion polymer) requires different solvents to obtain the desired solubility. The solvent may be volatile with a boiling point of 150° C. or less. In addition, the solvent should have relatively low toxicity and be removed from the dispersion to a level that is acceptable to The International Committee on Harmonization ("ICH") guidelines. Removal of solvent to this level may require a subsequent processing step, such as tray drying. Examples of suitable solvents include, but are not limited to, alcohols, such as methanol ("MeOH"), ethanol ("EtOH"), n-propanol, isopropanol ("IPA") and butanol; ketones, such as acetone, methyl ethyl ketone ("MEK") and methyl isobutyl ketone; esters, such as ethyl acetate ("EA") and propyl acetate; and various other solvents, such as tetrahydrofuran ("THF"), acetonitrile ("ACN"), methylene chloride, toluene and 1,1,1-trichloroethane. Lower volatility solvents, such as dimethyl acetate or dimethylsulfoxide ("DMSO"), may be used. Mixtures of solvents with water may also be used, so long as the dispersion polymer and the drug substance are sufficiently soluble to make the spray drying process practicable. Generally, due to the hydrophobic nature of low solubility drugs, non-aqueous solvents may be used, meaning the solvent comprises less than about 10 weight % water.

In certain embodiments, the suitable solvent is selected from MeOH and THF, and mixtures thereof. In certain embodiments, the suitable solvent is MeOH:THF solvent system of about 1:3. In certain embodiments, the suitable solvent is a 1:3 MeOH:THF solvent system.

In certain embodiments, the suitable solvent is selected from MeOH, THF and water, and mixtures thereof. In certain embodiments, the suitable solvent is selected from MeOH, THF and water. In certain embodiments, the suitable solvent is a THF:MeOH:water solvent system of about 80:10:10. In certain embodiments, the suitable solvent is a 80:10:10 THF:MeOH:water solvent system. In certain embodiments, the suitable solvent is a THF:MeOH:water solvent system of about 82:8:10. In certain embodiments, the suitable solvent is a 82:8:10 THF:MeOH:water solvent system. In certain embodiments, the suitable solvent is a THF:MeOH:water solvent system of about 82.2:8.2:9.6. In certain embodiments, the suitable solvent is a 82.2:8.2:9.6 THF:MeOH:water solvent system.

In certain embodiments, the amount of drug substance component in the solid dispersion ranges from about 0.1% to about 70% by weight relative to the dispersion polymer. In certain embodiments, the amount of drug substance component in the solid dispersion ranges from 0.1% to 70% by weight relative to the dispersion polymer.

In certain embodiments, the amount of drug substance component in the solid dispersion ranges from about 1% to about 60% by weight relative to the dispersion polymer. In certain embodiments, the amount of drug substance component in the solid dispersion ranges from 1% to 60% by weight relative to the dispersion polymer.

In certain embodiments, the amount of drug substance component in the solid dispersion ranges from about 5% to about 60% by weight relative to the dispersion polymer. In certain embodiments, the amount of drug substance component in the solid dispersion ranges from 5% to 60% by weight relative to the dispersion polymer.

In certain embodiments, the amount of drug substance component in the solid dispersion ranges from about 55% to about 65% by weight relative to the dispersion polymer. In certain embodiments, the amount of drug substance component in the solid dispersion ranges from 55% to 65% by weight relative to the dispersion polymer. In certain embodiments, the amount of drug substance component in the solid dispersion is about 60% by weight relative to the dispersion polymer. In certain embodiments, the amount of drug substance component in the solid dispersion is 60% by weight relative to the dispersion polymer.

In certain embodiments, the amount of drug substance component in the solid dispersion ranges from about 25% to about 35% by weight relative to the dispersion polymer. In certain embodiments, the amount of drug substance component in the solid dispersion ranges from 25% to 35% by weight relative to the dispersion polymer. In certain embodiments, the amount of drug substance component in the solid dispersion is about 30% by weight relative to the dispersion polymer. In certain embodiments, the amount of drug substance component in the solid dispersion is 30% by weight relative to the dispersion polymer.

In certain embodiments, the amount of drug substance component in the solid dispersion ranges from about 45% to about 55% by weight relative to the dispersion polymer. In certain embodiments, the amount of drug substance component in the solid dispersion ranges from 45% to 55% by weight relative to the dispersion polymer. In certain embodiments, the amount of drug substance component in the solid dispersion is about 50% by weight relative to the dispersion polymer. In certain embodiments, the amount of drug substance component in the solid dispersion is 50% by weight relative to the dispersion polymer.

In certain embodiments, the solid dispersion is an amorphous solid dispersion. In certain embodiments, the solid dispersion is administered orally. In certain embodiments, the solid dispersion is in a tablet. In certain embodiments, the amorphous solid dispersion is in a tablet.

In certain embodiments, the administration of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof is administered orally. In certain embodiments, the administration of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof is administered in the form of a tablet.

In certain embodiments, the treatment of brain cancer with N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof is in combination with another therapeutic agent. Such therapeutic agents are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, the therapeutic agent is selected from trastuzumab, capecitabine, bevacizumab, and taxanes. In certain embodiments, the therapeutic agent is selected from trastuzumab, capecitabine, bevacizumab, paclitaxel and docetaxel. In certain embodiments, the therapeutic agent is trastuzumab. In certain embodiments, the therapeutic agent is capecitabine. In certain embodiments, the therapeutic agent is bevacizumab. In certain embodiments, the therapeutic agent is paclitaxel. In certain embodiments, the therapeutic agent is docetaxel.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (24(44(4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for use in treating brain cancer, is used after previous treatment for cancer.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for use in treating brain cancer, is used after previous treatment for brain cancer. In certain embodiments, the previous treatment for brain cancer is selected from surgery, radiation therapy and chemotherapy or mixtures thereof. In certain embodiments, the previous treatment for brain cancer is selected from surgery, conventional external radiation therapy, three-dimensional conformal radiation therapy, intensity modulated radiation therapy, stereotactic radiosurgery, fractionated stereotactic radiation therapy, proton radiation therapy, internal or implant radiation therapy, temozolomide, bevacizumab, carmustine, lomustine, procarbazine, vincristine, tumor treating fields therapy, everolimus, procarbazine, lomustine, cisplatin, carboplatin and methotrexate or mixtures thereof.

In certain embodiments, the N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof for use in treating brain cancer, is used after previous treatment for breast cancer. In certain embodiments, the previous treatment for breast cancer is selected from surgery, sentinel lymph node biopsy followed by surgery, radiation therapy, chemotherapy, hormone therapy and targeted therapy. In certain embodiments, the previous treatment for breast cancer is selected from lumpectomy, partial mastectomy, segmental mastectomy, total mastectomy, modified radical mastectomy, external radiation, internal radiation, ado-trastuzumab emtansine, anastrozole, bevacizumab, capecitabine, carboplatin, cyclophosphamide, darbepoetin alfa, daunorubicin, denosumab, docetaxel, doxorubicin, epirubicin, epoetin alfa, eribulin, everolimus, exemestane, filgrastim, fluorouracil, fluoxymesterone, fulvestrant, gemcitabine, goserelin, ixabepilone, lapatinib, letrozole, leucovorin, leuprolide, megestrol, methotrexate, mitoxantrone, mutamycin, paclitaxel, paclitaxel albumin-stabilized nanoparticle formulation, pamidronate, pegfilgrastim, pertuzumab, raloxifene, tamoxifen, thiotepa, toremifene, trastuzumab, trastuzumab emtansine, triptorelin, vincristine, vinorelbine and zoledronic acid or mixtures thereof. In certain embodiments, the previous treatment for breast cancer is selected from bevacizumab, capecitabine, carboplatin, cyclophosphamide, daunorubicin, docetaxel, doxorubicin, epirubicin, eribulin, everolimus, fluorouracil, gemcitabine, ixabepilone, methotrexate, mitoxantrone, mutamycin, paclitaxel, paclitaxel albumin-stabilized nanoparticle formulation, tamoxifen, trastuzumab, trastuzumab emtansine, vincristine and vinorelbine or mixtures thereof.

In another embodiment, a method of treating brain cancer in a mammal comprising administering a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol to the mammal is provided.

In another embodiment, a method of treating brain cancer in a patient having brain cancer comprising administering a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol to the patient is provided.

In another embodiment, a method of treating or preventing brain cancer in a mammal in need of such treatment, wherein the method comprises administering to said mammal a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol.

In another embodiment, a method of treating brain cancer in a mammal using (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol comprising administering an effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine to the mammal is provided.

In another embodiment, a method of treating brain cancer using (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol in a patient having brain cancer comprising administering an effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine to the patient is provided.

In another embodiment, a method of treating or preventing local or metastatic brain cancer that is caused by ErbB2 over-expression or amplification using (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol in a mammal in need of such treatment, wherein the method comprises administering to the mammal an effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is provided.

In certain embodiments, the effective amount is a therapeutically effective amount.

Another embodiment provides the use of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol in the manufacture of a medicament for the treatment of brain cancer.

Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005.

The pharmaceutical compositions may also include one or more additional components, such as buffers, dispersion agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug, i.e., a compound described herein or pharmaceutical composition thereof, or aid in the manufacturing of the pharmaceutical product, i.e., medicament (see Ansel; Gennaro; and Rowe above). The components of the pharmaceutical composition should be pharmaceutically acceptable.

Certain embodiments provide a pharmaceutical composition for the treatment of brain cancer comprising:
  (a) about 1 to about 70 weight % of a solid dispersion of N4-(4-([1,2,4]triazolo[1,5a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
  (b) about 0.1 to about 20 weight % of a disintegrant;

(c) about 0.1 to about 25 weight % of an osmogen;
(d) about 0.1 to about 10 weight % of a glidant;
(e) about 0.1 to about 10 weight % of a lubricant; and
(f) about 0.1 to about 25 weight % of a binder/diluent.

In a further embodiment, the pharmaceutical composition for the treatment of brain cancer comprises:
(a) 1 to 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 0.1 to 20 weight % of a disintegrant;
(c) 0.1 to 25 weight % of an osmogen;
(d) 0.1 to 10 weight % of a glidant;
(e) 0.1 to 10 weight % of a lubricant; and
(f) 0.1 to 25 weight % of a binder/diluent.

Certain embodiments provide a pharmaceutical composition for the treatment of brain cancer comprising:
(a) about 25 to about 60 weight % of a solid dispersion of N4-(4-([1,2,4]triazolo[1,5a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 5 to about 15 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a binder/diluent.

In a further embodiment, the pharmaceutical composition for the treatment of brain cancer comprises:
(a) 25 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 5 to 15 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a binder/diluent.

Certain embodiments provide a pharmaceutical composition for the treatment of brain cancer comprising:
(a) about 40 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 5 to about 15 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a binder/diluent.

In a further embodiment, the pharmaceutical composition for the treatment of brain cancer comprises:
(a) 40 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 5 to 15 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a binder/diluent.

Certain embodiments provide a pharmaceutical composition for the treatment of brain cancer comprising:
(a) about 1 to about 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 0.1 to about 20 weight % of a disintegrant;
(c) about 0.1 to about 25 weight % of an osmogen;
(d) about 0.1 to about 10 weight % of a glidant;
(e) about 0.1 to about 10 weight % of a lubricant; and
(f) about 0.1 to about 25 weight % of a filler.

In a further embodiment, the pharmaceutical composition for the treatment of brain cancer comprises:
(a) 1 to 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 0.1 to 20 weight % of a disintegrant;
(c) 0.1 to 25 weight % of an osmogen;
(d) 0.1 to 10 weight % of a glidant;
(e) 0.1 to 10 weight % of a lubricant; and
(f) 0.1 to 25 weight % of a filler.

Certain embodiments provide a pharmaceutical composition for the treatment of brain cancer comprising:
(a) about 25 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 1 to about 10 weight % of a disintegrant;
(c) about 15 to about 25 weight % of an osmogen;
(d) about 0.1 to about 3 weight % of a glidant;
(e) about 0.1 to about 3 weight % of a lubricant; and
(f) about 10 to about 25 weight % of a filler.

In a further embodiment, the pharmaceutical composition for the treatment of brain cancer comprises:
(a) 25 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 1 to 10 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a filler.

Certain embodiments provide a pharmaceutical composition for the treatment of brain cancer comprising:
(a) about 40 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 1 to about 10 weight % of a disintegrant;
(c) about 15 to about 25 weight % of an osmogen;
(d) about 0.1 to about 3 weight % of a glidant;
(e) about 0.1 to about 3 weight % of a lubricant; and about 10 to about 25 weight % of a filler.

In a further embodiment, the pharmaceutical composition for the treatment of brain cancer comprises:
(a) 40 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 1 to 10 weight % of a disintegrant;
(c) 15 to 25 weight % of an osmogen;
(d) 0.1 to 3 weight % of a glidant;
(e) 0.1 to 3 weight % of a lubricant; and
(f) 10 to 25 weight % of a filler.

In certain embodiments, the pharmaceutical composition for the treatment of brain cancer comprises a solid disepersion of N4-(4-([1,2,4]triazolo[1,5-a]pyridin-7-yloxy)-3-methylphenyl)-N6-(4,4-dimethyl-4,5-dihydrooxazol-2-yl)quinazoline- 4,6-diamine.

In certain embodiments, the pharmaceutical composition for the treatment of brain cancer comprises a solid disepersion of (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol.

In certain embodiments, the osmogen is selected from NaCl and KCl, and mixtures thereof.

In certain embodiments, the lubricant is magnesium stearate.

In certain embodiments, the glidant is colloidal silicon dioxide.

In certain embodiments, the binder/diluent is microcrystalline cellulose. In certain embodiments, the binder/diluent acts as both a binder and a diluent.

In certain embodiments, the binder is microcrystalline cellulose.

In certain embodiments, the diluent is microcrystalline cellulose.

In certain embodiments, the filler is lactose.

In certain embodiments, the disintegrant is selected from crospovidone and sodium bicarbonate (NaHCO₃), and mixtures thereof. In certain embodiments, the disintegrant is selected from crospovidone and sodium bicarbonate. In certain embodiments, the disintegrant is sodium bicarbonate. In certain embodiments, the disintegrant is crospovidone.

In certain embodiments, the composition contains sodium bicarbonate. N4-(4-([1,2,4]Triazolo[1,5-a]pyridin-7-yloxy)-3-methylphenyl)-N6-(4,4-dimethyl-4,5-dihydrooxazol-2-yl) quinazoline-4,6-diamine may slowly degrade, through hydrolysis or other means, to a carbamate impurity:

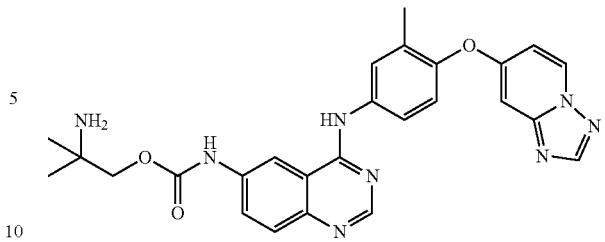

Sodium bicarbonate helps to slow the degradation to the carbamate impurity. Sodium bicarbonate also helps to provide consistent tablet disintegration when the tablets are exposed to different humidities.

Certain embodiments provide a pharmaceutical composition for the treatment of brain cancer comprising:
(a) N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) sodium bicarbonate.

Certain embodiments provide a pharmaceutical composition for the treatment of brain cancer comprising:
(a) about 1 to about 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) about 0.1 to about 30 weight % sodium bicarbonate.

In a further embodiment, the pharmaceutical composition for the treatment of brain cancer comprises:
(a) 1 to 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) 0.1 to 30 weight % sodium bicarbonate.

Certain embodiments provide a pharmaceutical composition for the treatment of brain cancer comprising:
(a) about 1 to about 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 0.1 to about 30 weight % sodium bicarbonate; and
(c) the remaining weight is other pharmaceutically acceptable excipients and carriers.

In a further embodiment, the pharmaceutical composition for the treatment of brain cancer comprises:
(a) 1 to 70 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;

(b) 0.1 to 30 weight % sodium bicarbonate; and
(c) the remaining weight is other pharmaceutically acceptable excipients and carriers.

Certain embodiments provide a pharmaceutical composition for the treatment of brain cancer comprising:
(a) about 25 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) about 1 to about 15 weight % of sodium bicarbonate.

In a further embodiment, the pharmaceutical composition for the treatment of brain cancer comprises:
(a) 25 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) 1 to 15 weight % of sodium bicarbonate.

Certain embodiments provide a pharmaceutical composition for the treatment of brain cancer comprising:
(a) about 25 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 1 to about 15 weight % of sodium bicarbonate; and
(c) the remaining weight is other pharmaceutically acceptable excipients and carriers.

In a further embodiment, the pharmaceutical composition for the treatment of brain cancer comprises:
(a) 25 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 1 to 15 weight % of sodium bicarbonate; and
(c) the remaining weight is other pharmaceutically acceptable excipients and carriers.

Certain embodiments provide a pharmaceutical composition for the treatment of brain cancer comprising:
(a) about 40 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) about 1 to about 15 weight % of sodium bicarbonate.

In a further embodiment, the pharmaceutical composition for the treatment of brain cancer comprises:
(a) 40 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof; and
(b) 1 to 15 weight % of sodium bicarbonate.

Certain embodiments provide a pharmaceutical composition for the treatment of brain cancer comprising:
(a) about 40 to about 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) about 1 to about 15 weight % of sodium bicarbonate;
(c) the remaining weight is other pharmaceutically acceptable excipients and carriers.

In a further embodiment, the pharmaceutical composition for the treatment of brain cancer comprises:
(a) 40 to 60 weight % of a solid dispersion of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof;
(b) 1 to 15 weight % of sodium bicarbonate;
(c) the remaining weight is other pharmaceutically acceptable excipients and carriers.

The pharmaceutical composition preferably contains a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof. However, in some embodiments, each individual dose contains a portion of a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine or (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol or mixtures thereof, such that multiple doses of the composition may be required (for example, two or more tablets are required for a therapeutically effective amount). Thus, in this application when it states that the pharmaceutical composition contains a therapeutically effective amount it means that the composition may be one dose (for example, one tablet) or multiple doses (for example, two tablets).

EXAMPLES

In the Examples described below, unless otherwise indicated all temperatures are set forth in degrees Celsius.

Example 1

Growth of NCI-N87 Gastric Carcinoma in Nude Mice Implanted Intracranially

Tumor cells (NCI-N87 gastric carcinoma cells, NCI, Bethesda, Md.) were implanted in nude BALB/c female mice (Charles River Laboratories International, Inc.) via intracranial injection directly into the brain. The mice were separated into four groups (N=5) and were injected with vehicle (saline), $1 \times 10^5$ tumor cells, $2.5 \times 10^5$ tumor cells, or $5 \times 10^5$ tumor cells. The results are shown in FIG. 1. Brain tumor cell burden was associated with decreased survival in the NCI-N87 model.

In a pilot study using $^{14}C$ albumin as the tracer and mannitol as the positive control for blood brain barrier (BBB) disruption, it was confirmed that the intracranial inoculation procedure did not mechanically disrupt the blood brain barrier.

Example 2

Figure 2:
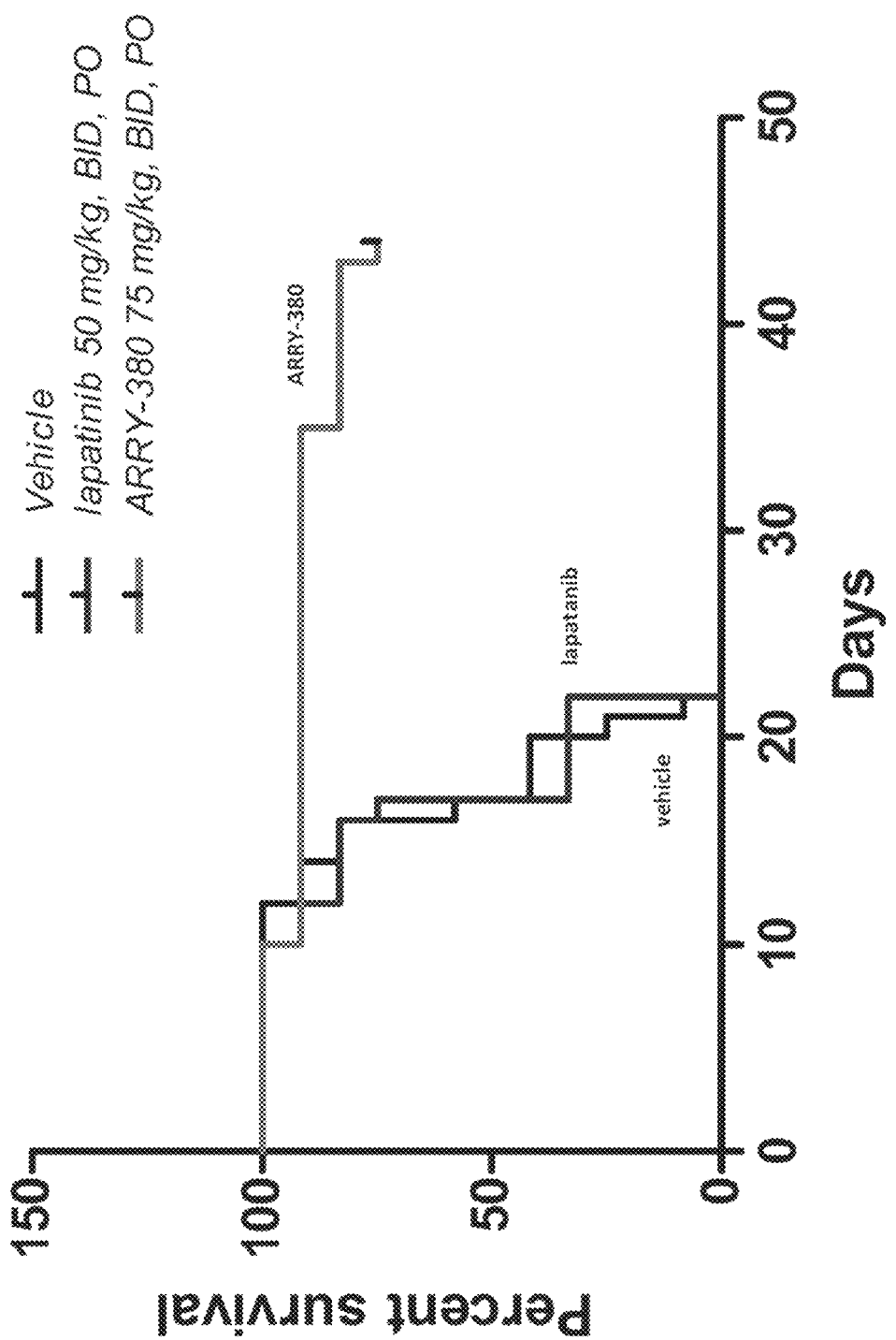
FIG. 2 shows the results of xenograft growth study of NCI-N87 cells implanted intracranially in mice.
Figure 3:
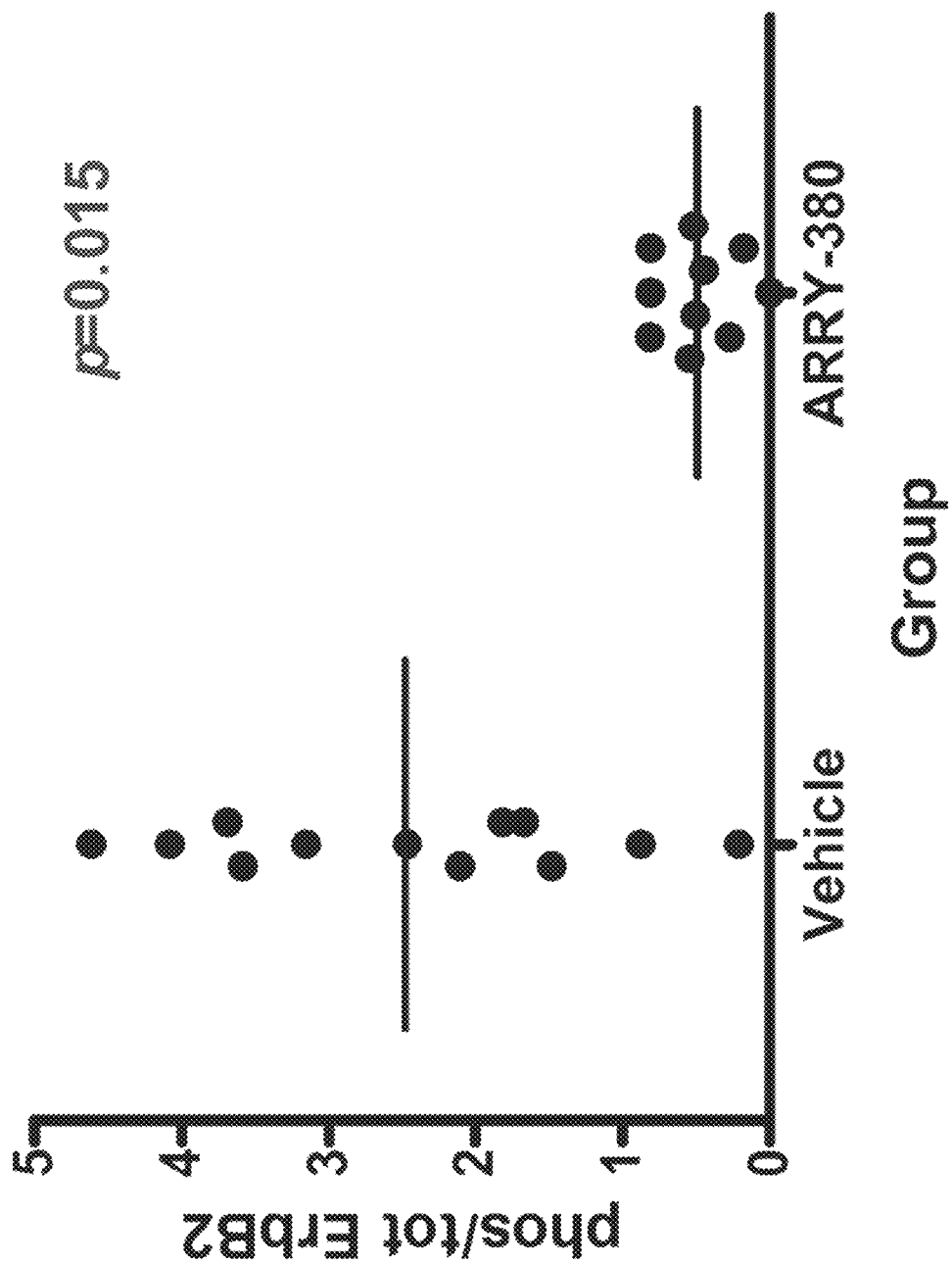
FIG. 3 shows the results of xenograft growth study of NCI-N87 cells implanted intracranially in mice.

Inhibition of NCI-N87 Gastric Carcinoma Xenograft Growth in Mice Implanted Intracranially Anesthetized nude BALB/c female mice (Taconic Laboritories Inc., Germantown, N.Y.) were inoculated with human tumor cells (NCI-N87 gastric carcinoma cells, NCI, Bethesda, Md.) intracranially at lamba suture. $5 \times 10^5$ cells in saline were implanted via intracranial injection. The mice were separated into three groups (N=12); vehicle (acidified 30% Captisol®, pH about 4.5), 50 mg/kg lapatanib PO BID (30% Captisol®), and 75 mg/kg N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine PO BID (acidified 30% Captisol®, pH about 4.5). Dosing began two days after implantation. The dose may have been reduced as necessary if drug-related weight loss (approximately 5%) was observed. The mice were monitored twice daily for general health and behavioral/neurological effects, and body weights (BW) were determined twice weekly. At first sign of neurological problem or body weight loss of greater than 20%, the mice were euthanized by $CO_2$ inhalation. Brain and plasma were collected for analyses. FIG. 2 shows the percentage of surviving mice. FIG. 3 shows that N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine significantly decreases phospho-ErbB2/total ErbB2 in the brain.

Example 3

Brain Pharmacokinetic (PK) Study in Mice

Nude female BALB/c mice were administered a single PO dose (dose volume 10 mL/kg) of lapatanib (50 mg/kg, 30% Captisol®) and N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (75 mg/kg, 30% Captisol, weigh out compound and add 30% Captisol® to give 7.5 mg/mL solution, then add 5 N HCl in 200 μL increments until it forms a clear, yellow solution). The mice were separated into groups and their PK was studied at 4 time points (0.5, 1, 2 and 4 hours, 4 mice per group per timepoint). The animals were euthanized by $CO_2$ inhalation at the time points. Whole blood was drawn (300 μL) by cardiac puncture and plced in an eppendorf tube containing ethylenediaminetetraacetic acid ("EDTA") (37.5 1.5%). The samples were centrifuged, and the plasma was decanted and frozen at −20° C. until delivered to analytical chemistry. The brains were collected. The animals were perfused with 5-10 mL of saline, and the brains were removed, weighed and placed into a fast prep tube for DMPK analysis.

Figure 4:
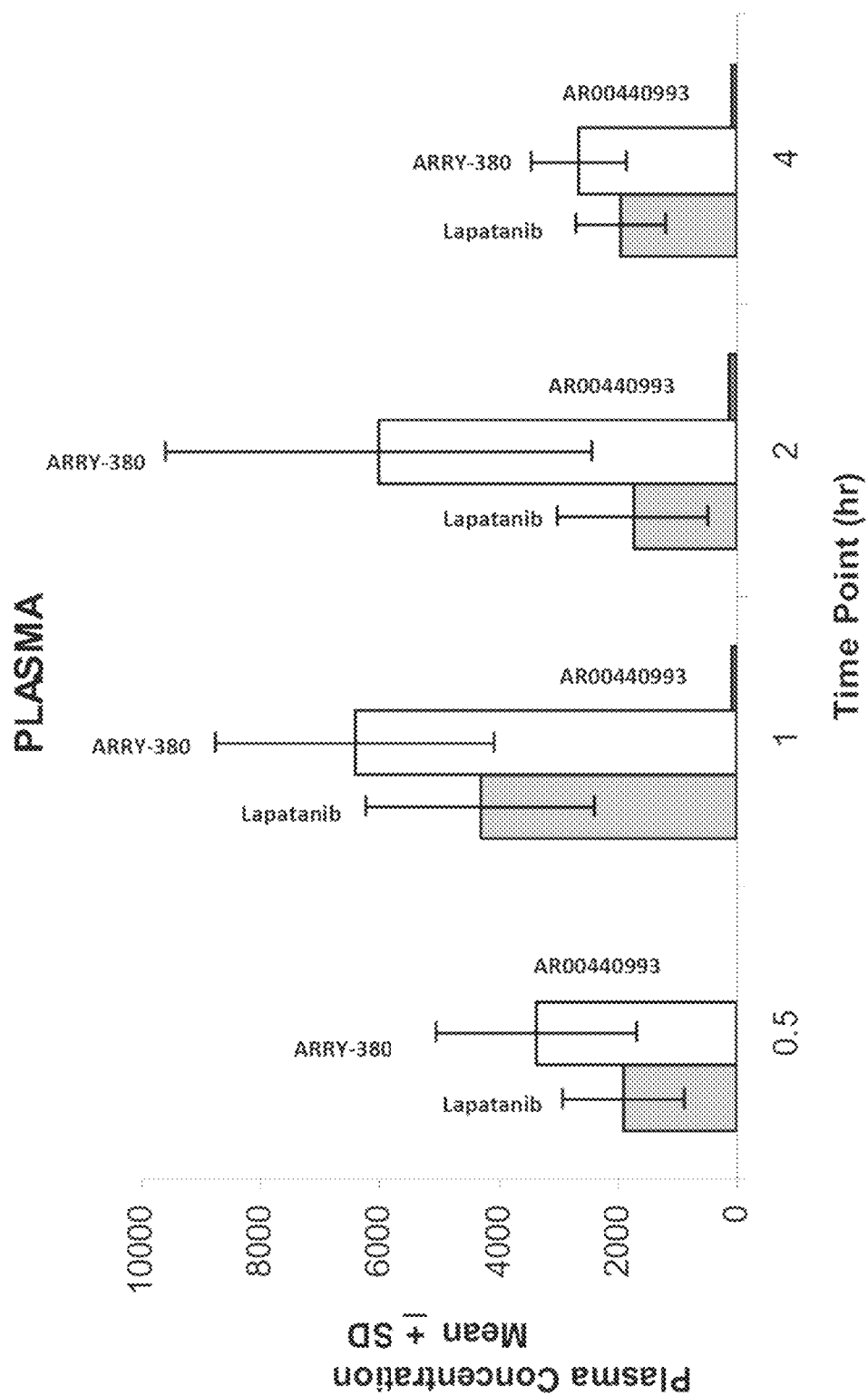
FIG. 4 shows the plasma results of brain pharmacokinetic study in mice.
Figure 5:
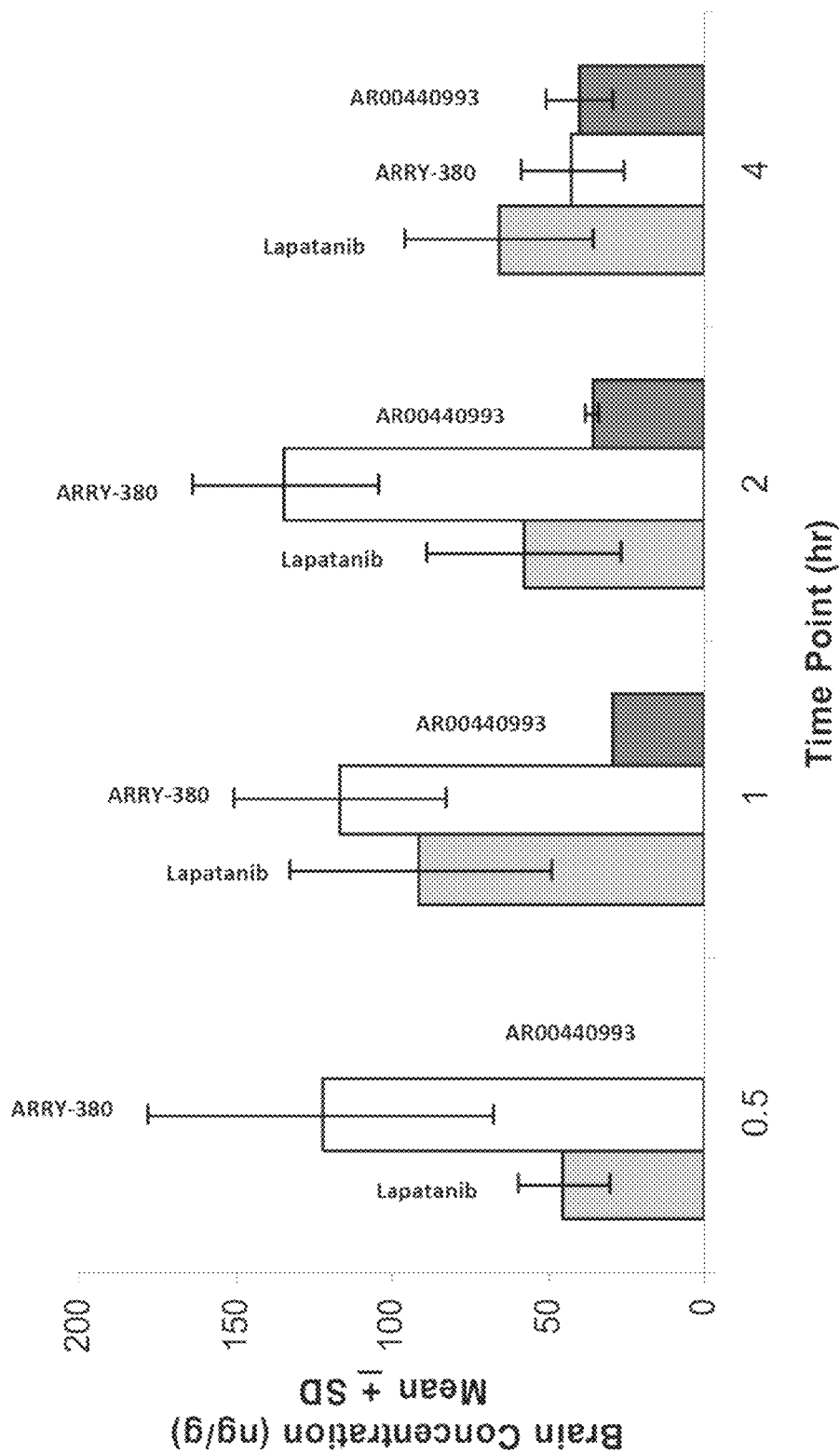
FIG. 5 shows the brain results of brain pharmacokinetic study in mice.

The brain penetration of (2-((4-((4-([1,2,4]triazolo[1,5-a]pyridin-7-yloxy)-3-methylphenyl)amino)quinazolin-6-yl)amino)-4-methyl-4,5-dihydrooxazol-4-yl)methanol was significantly higher than lapatanib or N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine. The plasma concentration (μg/mL) of the compounds is shown in FIG. 4 and Table 1. The brain concentration (ng/g) of the compounds is shown in FIG. 5 and Table 2. The brain:plasma ratio results are shown in Table 3.

TABLE 1

| Time Point | Average Plasma Concentration (μg/mL) | | |
|---|---|---|---|
| (hour) | Lapatanib | ARRY-380 | AR00440993 |
| 0.5 | 1913.75 | 3350.00 | 20.20 |
| 1 | 4310.00 | 6417.50 | 67.33 |
| 2 | 1743.75 | 6012.50 | 134.40 |
| 4 | 1942.50 | 2640.00 | 70.43 |

TABLE 2

| Time Point | Average Brain Concentration (ng/g) | | |
|---|---|---|---|
| (hour) | Lapatanib | ARRY-380 | AR00440993 |
| 0.5 | 44.92 | 122.38 | BLQ |
| 1 | 90.77 | 116.44 | 28.95 |
| 2 | 57.36 | 134.15 | 35.84 |
| 4 | 65.43 | 42.14 | 39.96 |

TABLE 3

| Time Point (hour) | Lapatanib | ARRY-380 | AR00440993 |
|---|---|---|---|
| 0.5 | 0.026 | 0.048 | — |
| 1 | 0.022 | 0.048 | 2.083 |
| 2 | 0.039 | 0.021 | 0.480 |
| 4 | 0.038 | 0.019 | 1.311 |

Example 4

Figure 6:
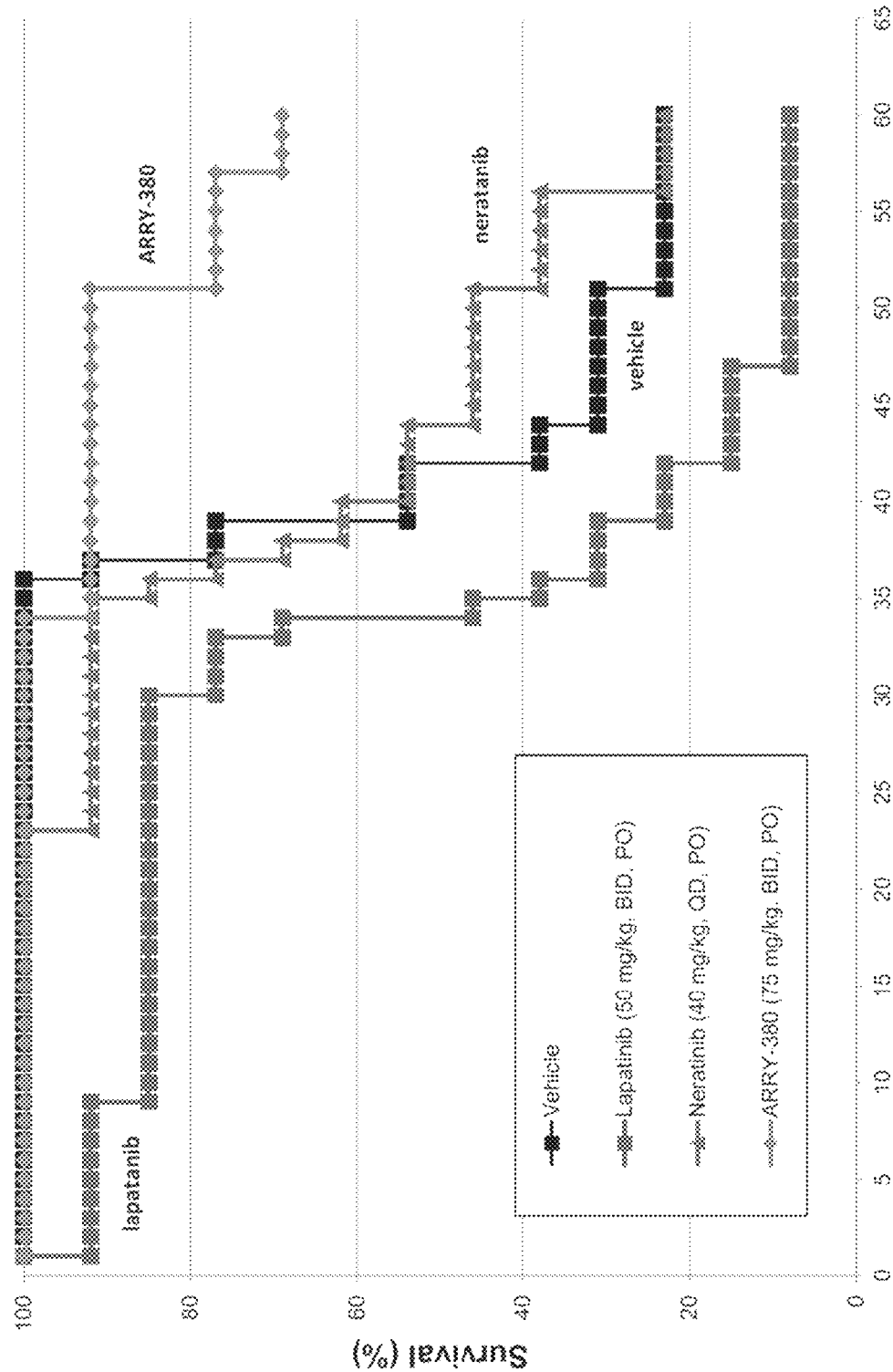
FIG. 6 shows the results of xenograft growth study of BT474 cells implanted intracranially in mice.

Inhibition of BT474 Breast Carcinoma Xenograft Growth in Mice Implanted Intracranially Nude NCr female mice (Taconic Laboritories Inc., Germantown, NY) were split into four groups (N=13). 17β-estradiol (0.5 mg)/progesterone (10 mg) pellets (35-day release) were implanted 1 day prior to BT-474 tumor cell inoculation. Tumor cells ($1 \times 10^6$ BT474 breast carcinoma cells, ATCC, Manassas, Va.) were implanted into the mice via intracranial injection directly into the brain. Treatment with vehicle or drugs began 2 days post-tumor cell implantation. The mice were administered vehicle (acidified 30% Captisol®, pH about 4.5, 10 mL/kg, PO, BID), lapatanib (50 mg/kg, PO, BID, 30% Captisol®), neratinib (40 mg/kg, QD, PO, acidified 30% Captisol®) and N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (75 mg/kg, PO, BID, 30% Captisol, weigh out compound and add 30% Captisol® to give 7.5 mg/mL solution, then add 5 N HCl in 200 μL increments until it forms a clear, yellow solution). The mice were monitored daily for general health and behavioral/neurological effects, and body weights were determined twice weekly. At first sign of neurological problem or body weight loss of greater than 20%, the mice were euthanized by $CO_2$ inhalation. Brain and plasma were collected for analyses. FIG. 6 shows the percentage of surviving mice.

Example 5

Anti-Tumor Efficacy on N87 Human Gastric Cancer in Murine Xenograft Model

Figure 7:
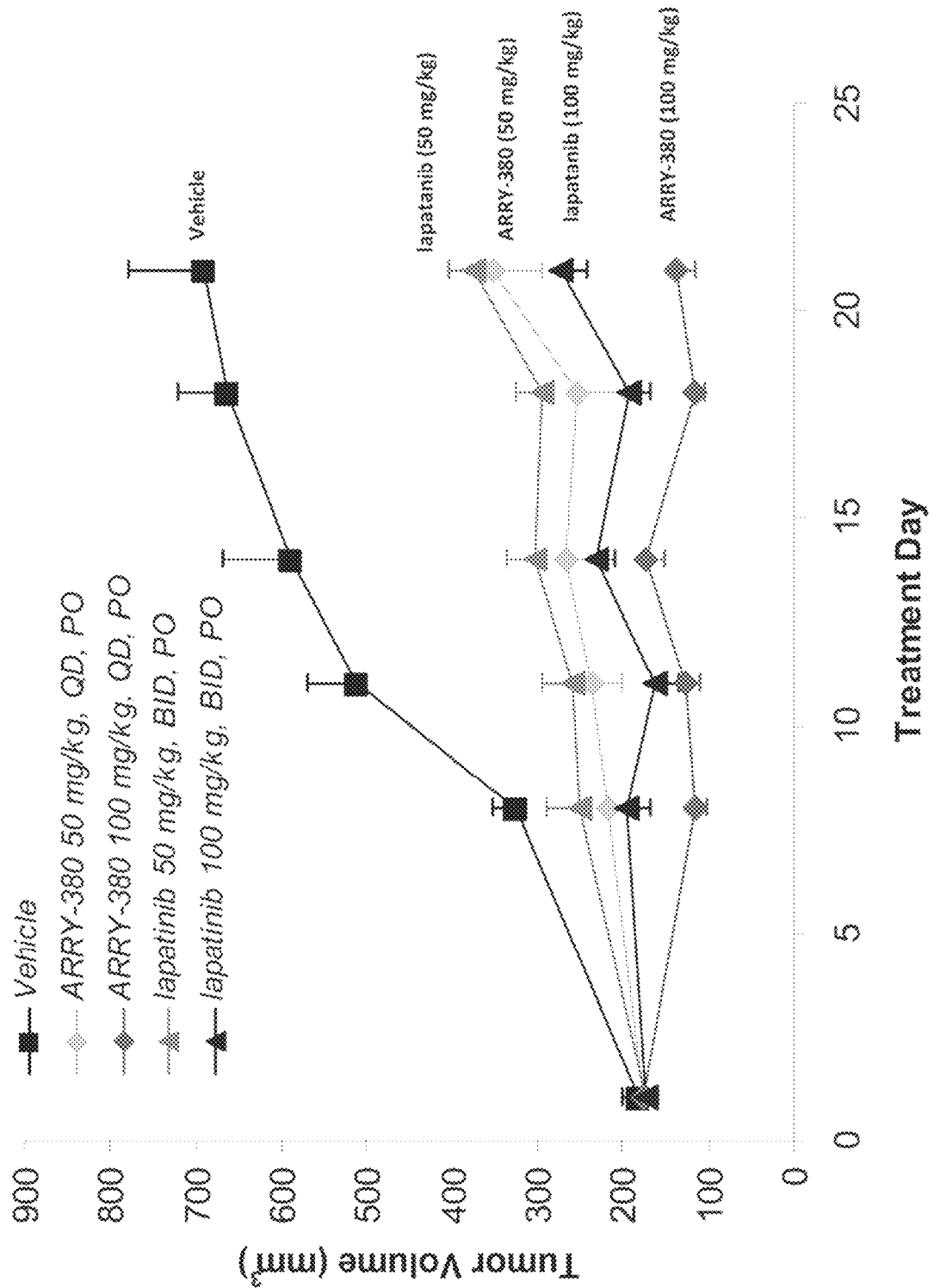
FIG. 7 shows the results of xenograft growth study of NCI-N87 cells implanted subcutaneously in mice.

Nude nu/nu female mice (NCI, Bethesda, Md.) were split into five groups (N=8). Tumor cells (NCI-N87 gastric carcinoma cells, NCI, Bethesda, Md. 1×10$^7$) were implanted into the mice via subcutaneous injection (100 µL) directly on the right flank. To ensure good tumor take, the cells should be greater than 90% viable (thus, the intitial cell suspension of 1×10$^7$ cells/mL were injected for 1×10$^6$ cells injected/100 The tumors were allowed to grow to 150±50 mm$^3$. The tumor size was measured, and the mice were weighed. The mice were administered vehicle (30% Captisol®, 150 g in 500 mL DI water, PO, BID), lapatanib (50 mg/kg, PO, BID, 30% Captisol®), lapatanib (100 mg/kg, PO, BID, 30% Captisol®), N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine (50 mg/kg, PO, QD, 30% Captisol) and N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (100 mg/kg, PO, QD, 30% Captisol). The tumor volume was measured. The number of partial responses in the mice was as follows: lapatanib (50 mg/kg) 0, lapatanib (100 mg/kg) 1, ARRY-380 (50 mg/kg) 1, ARRY-380 (100 mg/kg) 4. The results are shown in FIG. 7.

Example 6

30% Solid Dispersion Using PVP-VA

A solid dispersion was prepared containing 30 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and PVP-VA using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 19.6 g (87.7% yield) of the solid dispersion. Physicochemical analysis results are in Table 4. Residual solvent analysis showed that the dispersion had less than 0.5% THF and no detectable MeO H.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 63.46 µg/mL and 245.05 µg/mL*hr, respectively. The Cmax and AUC for the free drug species was 52.50 µg/mL and 204.12 µg/mL*hr, respectively.

Example 7

30% Solid Dispersion Using Eudragit

A solid dispersion was prepared containing 30 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and Eudragit L100 using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 18.6 g (82.7% yield) of the solid dispersion. Physicochemical analysis results are in Table 4. Residual solvent analysis showed that the dispersion had about 4.5% THF and no detectable MeOH.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 22.70 µg/mL and 71.06 µg/mL*hr, respectively. The Cmax and AUC for the free drug species was 9.26 µg/mL and 35.49 µg/mL*hr, respectively.

Example 8

30% Solid Dispersion Using HPMCP

A solid dispersion was prepared containing 30 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and HPMCP H-55 using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 20.3 g (90.3% yield) of the solid dispersion. Physicochemical analysis results are in Table 4. Residual solvent analysis showed that the dispersion had less than 0.5% THF and no detectable MeOH.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 25.00 µg/mL and 96.66 µg/mL*hr, respectively. The Cmax and AUC for the free drug species was 16.15 µg/mL and 56.81 µg/mL*hr, respectively.

Example 9

30% Solid Dispersion Using CAP

A solid dispersion was prepared containing 30 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and CAP using a Buchi B-290 mini spray drier. The solid dispersion was spray dried from a MeOH:THF (1:3) solvent system, a 5% spray solution concentration, an inlet temperature of 100° C. at a flow rate of 22 mL/minute, drying gas flow rate of 35 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 20.0 g (90.4% yield) of the solid dispersion. Physicochemical analysis results are in Table 4. Residual solvent analysis showed that the dispersion had less than 0.5% THF and no detectable MeOH.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 11.62 µg/mL and 36.69 µg/mL*hr, respectively. The Cmax and AUC for the free drug species was 5.64 µg/mL and 20.58 µg/mL*hr, respectively.

Example 10

30% Solid Dispersion Using HPMCAS

A solid dispersion was prepared containing 30 weight percent N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and HPMCAS Grade M using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 163.19 mg (48.3% yield) of the solid dispersion. Physicochemical analysis results are in Table 4. Residual solvent analysis showed that the dispersion had less than 0.5% THF and no detectable MeOH.

Dissolution testing was performed at a pH of 6.5 in phosphate buffer. The solid dispersion was suspended in $H_2O$ and added directly to the buffer solution at 37° C. The dissolution profile was collected over a period of about 240 minutes. The Cmax and AUC for the total drug species (colloidal+free) was 19.04 µg/mL and 68.09 µg/mL*hr, respectively. The Cmax and AUC for the free drug species was 13.50 µg/mL and 51.74 µg/mL*hr, respectively.

TABLE 4

| Example | Polymer | API: Polymer | HPLC (area %) | $T_g$ (° C.) | TGA wt loss (%) | % THF (w/w) | Hygroscopicity (% wt change at 80% RH) |
|---|---|---|---|---|---|---|---|
| REF | | | 99.39 | | 4.9 | | <1% |
| 6 | PVP-VA | 3:7 | 99.45 | 117 | 2.3 | 0.5 | 14.4 |
| 7 | Eudragit L100 | 3:7 | 98.63 | 116 | 5.9 | 4.5 | 7.5 |
| 8 | HPMCP H-55 | 3:7 | 97.30 | 149 | 1.7 | 0.3 | 7.5 |
| 9 | CAP | 3:7 | 95.45 | 179 | 1.9 | 0.5 | 7.8 |
| 10 | HPMCAS | 3:7 | | 113 | NA | NA | NA |

Example 11

60% Solid Dispersion Using PVP-VA

A solid dispersion was prepared containing 60 weight percent N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and PVP-VA using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 135.0 mg (88.2% yield) of the solid dispersion.

Dissolution testing was performed at a pH of 6.5 in phosphate buffer. The solid dispersion was suspended in $H_2O$ and added directly to the buffer solution at 37° C. The dissolution profile was collected over a period of about 240 minutes. The Cmax and AUC for the total drug species (colloidal+free) was 34.80 µg/mL and 133.76 µg/mL*hr, respectively. The Cmax and AUC for the free drug species was 21.88 µg/mL and 84.43 µg/mL*hr, respectively.

Example 12

60% Solid Dispersion Using Eudragit

A solid dispersion was prepared containing 60 weight percent N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and Eudragit L100 using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 88.1 mg (52.4% yield) of the solid dispersion.

Dissolution testing was performed at a pH of 6.5 in phosphate buffer. The solid dispersion was suspended in $H_2O$ and added directly to the buffer solution at 37° C. The dissolution profile was collected over a period of about 240 minutes. The Cmax and AUC for the total drug species (colloidal+free) was 26.82 µg/mL and 84.49 µg/mL*hr, respectively. The Cmax and AUC for the free drug species was 9.85 µg/mL and 34.89 µg/mL*hr, respectively.

Example 13

60% Solid Dispersion Using HPMCP

A solid dispersion was prepared containing 60 weight percent N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and HPMCP H-55 using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m³/hour, nozzle pressure of 80 psig, nozzle gas flow of 0.66 m³/hour, and a 1.5 mm nozzle type. Secondary drying of the dispersion was done at 40° C. under vacuum for about 16 hours. The spray drying yielded 98.0 mg (58.0% yield) of the solid dispersion.

Dissolution testing was performed at a pH of 6.5 in phosphate buffer. The solid dispersion was suspended in $H_2O$ and added directly to the buffer solution at 37° C. The dissolution profile was collected over a period of about 240 minutes. The Cmax and AUC for the total drug species (colloidal+free) was 32.21 µg/mL and 38.28 µg/mL*hr, respectively. The Cmax and AUC for the free drug species was 9.96 µg/mL and 38.28 µg/mL*hr, respectively.

Example 14

60% Solid Dispersion Using CAP

A solid dispersion was prepared containing 60 weight percent N4-(4-([1,2,4]triazolo[1,5-a]pyridin-7-yloxy)-3- methylphenyl)-N6-(4,4-dimethyl-4,5-dihydrooxazol-2-yl) quinazoline-4,6-diamine and CAP using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 74.9 mg (44.6% yield) of the solid dispersion.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 51.98 µg/mL and 144.91 µg/mL*hr, respectively. The Cmax and AUC for the free drug species was 15.07 µg/mL and 59.69 µg/mL*hr, respectively.

Example 15

60% Solid Dispersion Using HPMCAS

A solid dispersion was prepared containing 60 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and HPMCAS Grade M using a Buchi B-290 mini spray drier. The solid dispersion was spray dried from a MeOH:THF (1:3) solvent system, a 5% spray solution concentration, an inlet temperature of 80° C. at a flow rate of 35 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 40° C. under vacuum for about 16 hours. The spray drying yielded 113.3 mg (67.2% yield) of the solid dispersion.

Dissolution testing was performed at a pH of 6.5 in phosphate buffer. The solid dispersion was suspended in H$_2$O and added directly to the buffer solution at 37° C. The dissolution profile was collected over a period of about 240 minutes. The Cmax and AUC for the total drug species (colloidal+free) was 26.45 µg/mL and 96.21 µg/mL*hr, respectively. The Cmax and AUC for the free drug species was 10.96 µg/mL and 42.83 µg/mL*hr, respectively.

Example 16

50% Solid Dispersion Using PVP-PA

A solid dispersion was prepared containing 50 weight percent N4-(4-([1,2,4]triazolo[1,5-a]pyridin-7-yloxy)-3-methylphenyl)-N6-(4,4-dimethyl-4,5-dihydrooxazol-2-yl) quinazoline-4,6-diamine and PVP-VA using a Buchi B-290 mini spray drier. The solid dispersion was spray dried from a MeOH:THF (1:3) solvent system, a 3.9% spray solution concentration, an inlet temperature of 100° C. at a flow rate of 30 mL/minute, drying gas flow rate of 40 m$^3$/hour, nozzle pressure of 80 psig, nozzle gas flow of 0.66 m$^3$/hour, and a 1.5 mm nozzle type. Secondary drying of the dispersion was done at 50° C. under vacuum for about 72 hours. The spray drying yielded 28.7 g (72.7% yield) of the solid dispersion.

Example 17

Pharmaceutical Composition 1

Tablets containing the solid dispersions of any of Examples 6 to 16 may be prepared in a conventional manner comprising:

| Function | Ingredient | % of Blend |
| --- | --- | --- |
| API | Solid dispersion as prepared in Example 16 | 50 |
| Disintegrant | Crospovidone - Polyplasdone ® | 6 |
| Osmogen | NaCl | 5 |
| Osmogen | KCl | 5 |
| Glidant | Colloidal Silicon Dioxide | 0.5 |
| Lubricant Extragranular | Magnesium Stearate | 0.25 |
| Binder/Diluent | Microcrystalline cellulose - Avicel ® | 19.25 |
| Osmogen | NaCl | 4.625 |
| Osmogen | KCl | 4.625 |
| Disintegrant | Polyplasdone | 4 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 18

Pharmaceutical Composition 2

Tablets containing the solid dispersions of any of Examples 2 to 12 may be prepared in a conventional manner comprising:

| Function | Ingredient | % of Blend |
| --- | --- | --- |
| API | Solid dispersion as prepared in Example 16 | 50 |
| Disintegrant | Crospovidone - Polyplasdone ® | 6 |
| Disintegrant | NaHCO$_3$ | 3 |
| Osmogen | NaCl | 5 |
| Osmogen | KCl | 5 |
| Glidant | Colloidal Silicon Dioxide | 0.5 |
| Lubricant Extragranular | Magnesium Stearate | 0.25 |
| Binder/Diluent | Microcrystalline cellulose - Avicel ® | 16.25 |
| Osmogen | NaCl | 4.625 |
| Osmogen | KCl | 4.625 |
| Disintegrant | Polyplasdone | 4 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 19

Pharmaceutical Composition 3

Tablets containing the solid dispersions of any of Examples 2 to 12 may be prepared in a conventional manner comprising:

| Function | Ingredient | % of Blend |
|---|---|---|
| API | Solid dispersion as prepared in Example 16 | 50 |
| Disintegrant | Crospovidone - Polyplasdone ® | 6 |
| Osmogen | NaCl | 10.625 |
| Osmogen | KCl | 10.625 |
| Filler | Lactose | 21.25 |
| Glidant | Colloidal Silicon Dioxide | 0.5 |
| Lubricant Extragranular | Magnesium Stearate | 0.25 |
| Glidant | Colloidal Silicon Dioxide | 0.5 |
| Lubricant | Magnesium Stearate | 0.25 |

In one preparation, tablets were made using OPADRY II 85F92727 at 3% by weight as a tablet coating. The tablets contained 150 mg of API.

Example 20

Stability Screen

A stability screen of the spray dried dispersions was completed at 40° C., 75% relative humidity under open conditions, in glass vials, over a period of 8 days. Results are shown in Table 5.

TABLE 5

| | HPLC Area % | | | |
|---|---|---|---|---|
| Time | Example 6 | Example 7 | Example 8 | Example 9 |
| Standard | 99.39 | 99.39 | 99.39 | 99.39 |
| As received | 99.45 | 98.63 | 97.30 | 95.45 |
| 4 days | 99.21 | 96.10 | 93.03 | 90.89 |
| 8 days | 99.35 | 93.16 | 86.63 | 87.15 |

The main degradant observed was a carbamate impurity, likely due to the acidic nature of some of these polymers. XRPD analysis over the course of the study showed no evidence of crystallization for any solid dispersion of Examples 6-9.

Example 21

N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine freebase hemi-ethanolate Step 1: (E)-N'-(2-Cyano-4-(3-(1-hydroxy-2-methylpropan-2-yl)thioureido) phenyl)-N,N-dimethylformimidamide was coupled with 4-([1,2,4]triazolo[1,5-a]pyridin-7-yloxy)-3-methylaniline in isopropyl acetate:acetic acid (65:35 v/v) at 45° C. to yield 1-(4-((4-([1,2,4]triazolo[1,5-a]pyridin-7-yloxy)-3-methylphenyl)amino)quinazolin-6-yl)-3-(1-hydroxy-2-methylpropan-2-yl)thiourea (91%).

Step 2: 1-(4-((4-([1,2,4]Triazolo[1,5-a]pyridin-7-yloxy)-3-methylphenyl) amino)quinazolin-6-yl)-3-(1-hydroxy-2-methylpropan-2-yl)thiourea was agitated in tetrahydrofuran under basic conditions (2.5N NaOH), followed by the addition of p-toluenesulfonyl chloride. Water was charged to yield N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine (96%) as a mixture of polymorphs (generally a mixture containing one or more of Form C, Form G hemi-THF, Form G mono-THF, Form M or Form P).

Step 3: N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine from Step 2 was triturated in ethanol at greater than 65° C. to provide N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine Form B Ethanol (89%).

Dissolution testing was performed at a pH of 6.5 in phosphate buffer. The crystals (particles) were suspended in $H_2O$ and added directly to the buffer solution at 37° C. The dissolution profile was collected over a period of about 240 minutes. The Cmax and AUC for the free drug species was 0.44 µg/mL and 5.49 µg/mL*hr, respectively.

Example 22

In Vivo Pharmacokinetics in Beagles

The solid dispersion of Example 6 was tested against a crystalline, micronized suspension formulation (d(v, 0.9)=3.0 µm) of Example 21 under normal fasted conditions, as well as with pretreatment using pentagastrin or famotidine. The solid dispersion of Example 6 was prepared as a suspension in water and administered orally. The micronized suspension of Example 21 was prepared as a suspension with SyrSpend® SF Dry reconstituted with water and administered orally. To reduce variability, beagles were crossed over from pentagastrin to famotidine after a 5 day washout period. Pentagastrin is a pH modifier to modify gastric pH to about 2 to 3, and famotidine is a pH modifier to modify gastric pH to about 5 to 7.5 (Zhou, Rong, et al. "pH-Dependent Dissolution in Vitro and Absorption in Vivo of Weakly Basic Drugs: Development of a Canine Model." Pharm. Res. Vol. 22, No. 2 (Feb. 2005): pp. 188-192). There were four beagles per group. Group A received pentagastrin pretreatment, the micronized suspension of Example 21, followed by a 5 day washout period, then famotidine pretreatment, and finally the micronized suspension of Example 21. Group B received pentagastrin pretreatment, the solid dispersion of Example 6, followed by a 5 day washout period, then famotidine pretreatment, and finally the solid dispersion of Example 6. Group C received the micronized suspension of Example 21, followed by a 5 day washout period, and finally the solid dispersion of Example 6. Results are shown in Table 6.

TABLE 6

| Pre-treatment | Dosing Formulation | $AUC_{inf}$ (µg*hr/mL) | $C_{max}$ (µg/mL) |
|---|---|---|---|
| Micronized | Suspension of Example 12 | 7.43 ± 1.77 | 1.88 ± 0.35 |
| None | Solid Dispersion of Example 1 | 10.0 ± 2.7 | 2.29 ± 0.54 |
| 6 µg/kg Pentagastrin | Micronized Suspension of Example 12 | 17.2 ± 2.7 | 3.29 ± 0.13 |
| | Solid Dispersion of Example 1 | 13.0 ± 3.6 | 3.12 ± 0.62 |
| 40 mg/kg Famotidine | Micronized Suspension of Example 12 | 1.74 ± 0.39 | 0.514 ± 0.092 |
| | Solid Dispersion of Example 1 | 6.32 ± 2.88 | 1.45 ± 0.54 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating brain metastases in a patient suffering from ErbB2 positive breast cancer with brain metastases, comprising administering to the patient a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine, in combination with trastuzumab and capecitabine.

2. The method of claim 1, wherein the patient has been previously treated for breast cancer.

3. The method of claim 2, wherein the patient has been previously treated with trastuzumab for breast cancer.

4. The method of claim 1, wherein N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is administered to the patient in an oral dosage form.

5. The method of claim 4, wherein the oral dosage form is administered from about 100 m to about 1600 m per day.

6. The method of claim 2, wherein N4-(4-((1,2,4]triazolo[1,5-a]pyridin-7-yloxy)-3-methylphenyl)-N6-(4,4-dimethy1-4,5-dihydrooxazol-2-yl)quinazoline-4,6-diamine is administered to the patient in an oral dosage form.

7. The method of claim 6, wherein the oral dosage form is administered to the patient from about 100 mg to about 1600 mg per day.

8. A method of treating a patient suffering from breast cancer with brain metastases, comprising administering to the patient a therapeutically effective amount of N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine, in combination with trastuzumab and capecitabine.

9. The method of claim 8, wherein the breast cancer is ErbB2 positive.

10. The method of claim 8, wherein the patient has been previously treated for breast cancer.

11. The method of claim 10, wherein the patient has been previously treated with trastuzumab for breast cancer.

12. The method of claim 8, wherein N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is administered to the patient in an oral dosage form.

13. The method of claim 12, wherein the oral dosage form is administered from about 100 mg to about 1600 mg per day.

14. The method of claim 9, wherein N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine is administered to the patient in an oral dosage form.

15. The method of claim 14, wherein the oral dosage form is a solid dispersion oral dosage form.

16. The method of claim 15, wherein the tablet is administered to the patient from about 100 mg to about 1600 mg per day.

* * * * *

UNITED STATES PATENT AND TRADEMARK OFFICE
CERTIFICATE OF CORRECTION

| | |
|---|---|
| PATENT NO. | : 11,504,370 B2 |
| APPLICATION NO. | : 16/402068 |
| DATED | : November 22, 2022 |
| INVENTOR(S) | : Patrice A. Lee, Shannon L. Winski and Kevin Koch |

It is certified that error appears in the above-identified patent and that said Letters Patent is hereby corrected as shown below:

In the Claims

Column 31, Line 27 please delete "about 100 m to about 1600 m per day." and insert -- "about 100 mg to about 1600 mg per day. -- therefor.

Signed and Sealed this
Twenty-sixth Day of December, 2023

Katherine Kelly Vidal
Director of the United States Patent and Trademark Office